United States Patent
Vayser et al.

(10) Patent No.: US 10,568,712 B2
(45) Date of Patent: *Feb. 25, 2020

(54) ILLUMINATED TELESCOPING CANNULA

(71) Applicant: Invuity, Inc., San Francisco, CA (US)

(72) Inventors: Alex Vayser, Mission Viejo, CA (US); Kenneth B. Trauner, San Francisco, CA (US); Jonathan G. Gasson, Novato, CA (US); Thomas L. Grey, San Marcos, CA (US)

(73) Assignee: Invuity, Inc., San Francisco, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 15/384,776

(22) Filed: Dec. 20, 2016

(65) Prior Publication Data

US 2017/0100022 A1    Apr. 13, 2017

Related U.S. Application Data

(63) Continuation of application No. 14/635,996, filed on Mar. 2, 2015, which is a continuation of application
(Continued)

(51) Int. Cl.
*A61B 90/30* (2016.01)
*A61B 1/06* (2006.01)
(Continued)

(52) U.S. Cl.
CPC .......... *A61B 90/30* (2016.02); *A61B 1/00096* (2013.01); *A61B 1/00135* (2013.01);
(Continued)

(58) Field of Classification Search
CPC .............. A61B 90/30; A61B 2090/306; A61B 2090/309; A61B 1/00135; A61B 1/06;
(Continued)

(56) References Cited

U.S. PATENT DOCUMENTS

| 1,246,340 A | 11/1917 | Smit |
| 2,482,971 A | 9/1949 | Golson |

(Continued)

FOREIGN PATENT DOCUMENTS

| DE | 4238977 A1 | 5/1994 |
| EP | 0101781 A1 | 3/1984 |

(Continued)

OTHER PUBLICATIONS

European search report dated Aug. 9, 2012 for EP 12171467.9.
(Continued)

*Primary Examiner* — John P Leubecker
(74) *Attorney, Agent, or Firm* — McDonnell Boehnen Hulbert & Berthoff LLP

(57) ABSTRACT

An illumination system includes a surgical tool and an attachable cannula comprising a transparent or semi-transparent material capable of carrying light from the proximal end to the distal end of the cannula, thereby illuminating the surgical field through components that do not occupy space that may otherwise be used for optics of the tool. The illumination system further comprises one or more illumination sources disposed at the proximal end. The illumination source may be optically coupled with the cannula at the hub or other appropriate location. The cannula comprises a sterilizable polymer which functions as a waveguide. A waveguide is a material medium that confines and guides light. When in use, the light source connected to the hub provides light which may be guided to the distal end of the cannula or any other suitable location. Thus, the sheath provides structure-guided illumination resulting in the illumination of the surgical site.

20 Claims, 16 Drawing Sheets

Related U.S. Application Data

No. 12/188,055, filed on Aug. 7, 2008, now Pat. No. 9,005,115, which is a continuation-in-part of application No. 11/715,247, filed on Mar. 6, 2007, now Pat. No. 7,901,353, which is a continuation-in-part of application No. 11/397,446, filed on Apr. 3, 2006, now Pat. No. 7,510,524.

(60) Provisional application No. 60/724,717, filed on Oct. 7, 2005, provisional application No. 60/668,442, filed on Apr. 4, 2005.

(51) Int. Cl.
*A61B 1/00* (2006.01)
*A61B 1/317* (2006.01)
*G02B 23/24* (2006.01)
*A61B 1/32* (2006.01)
*A61B 17/34* (2006.01)
*A61B 17/02* (2006.01)
*A61B 1/07* (2006.01)
*A61B 1/313* (2006.01)
*G02B 6/42* (2006.01)

(52) U.S. Cl.
CPC .......... *A61B 1/0607* (2013.01); *A61B 1/0669* (2013.01); *A61B 1/0676* (2013.01); *A61B 1/07* (2013.01); *A61B 1/317* (2013.01); *A61B 1/3132* (2013.01); *A61B 1/32* (2013.01); *A61B 17/0293* (2013.01); *A61B 17/3421* (2013.01); *A61B 17/3423* (2013.01); *G02B 6/4285* (2013.01); *G02B 23/2469* (2013.01); *A61B 2017/3443* (2013.01); *A61B 2017/3445* (2013.01); *A61B 2017/3488* (2013.01); *A61B 2090/306* (2016.02)

(58) Field of Classification Search
CPC ....... A61B 1/0607; A61B 1/0684; A61B 1/07; A61B 1/3132; A61B 17/3421; A61B 17/3423
See application file for complete search history.

(56) References Cited

U.S. PATENT DOCUMENTS

| | | |
|---|---|---|
| 2,843,112 A | 7/1958 | Miller |
| 3,075,516 A | 1/1963 | Strauch |
| 3,261,349 A | 7/1966 | Wallace |
| 3,413,067 A | 11/1968 | Froio |
| 3,498,286 A | 3/1970 | Polanyi et al. |
| 3,572,325 A | 3/1971 | Bezell et al. |
| 3,638,644 A | 2/1972 | Reick |
| 3,641,332 A | 2/1972 | Reick et al. |
| 3,770,342 A | 11/1973 | Dudragne |
| 3,779,628 A | 12/1973 | Kapron et al. |
| 3,889,661 A | 6/1975 | Fiore |
| 3,890,960 A | 6/1975 | Wunsch et al. |
| 4,215,678 A | 8/1980 | Erfurt et al. |
| 4,226,228 A | 10/1980 | Shin et al. |
| 4,300,541 A | 11/1981 | Burgin |
| 4,306,546 A | 12/1981 | Heine et al. |
| 4,469,554 A | 9/1984 | Turner |
| 4,519,385 A | 5/1985 | Atkinson et al. |
| 4,526,573 A | 7/1985 | Lester et al. |
| 4,562,832 A | 1/1986 | Wilder et al. |
| 4,589,404 A | 5/1986 | Barath et al. |
| 4,592,344 A | 6/1986 | Scheer |
| 4,593,973 A | 6/1986 | Yoshida et al. |
| 4,597,030 A | 6/1986 | Brody et al. |
| 4,605,990 A | 8/1986 | Wilder et al. |
| 4,617,013 A | 10/1986 | Betz |
| 4,643,172 A | 2/1987 | Taff et al. |
| 4,697,578 A | 10/1987 | Burgin |
| 4,736,733 A | 4/1988 | Adair |
| 4,768,858 A | 9/1988 | Hussein |
| 4,776,659 A | 10/1988 | Mruk |
| 4,792,692 A | 12/1988 | Herold et al. |
| 4,805,984 A | 2/1989 | Cobb, Jr. |
| 4,807,599 A | 2/1989 | Robinson et al. |
| 4,819,620 A | 4/1989 | Okutsu |
| 4,842,356 A | 6/1989 | Mori |
| 4,872,837 A * | 10/1989 | Issalene ............ A61C 1/088 433/29 |
| 4,906,070 A | 3/1990 | Cobb, Jr. |
| 4,961,617 A | 10/1990 | Shahidi et al. |
| 5,035,232 A | 7/1991 | Lutze et al. |
| 5,136,480 A | 8/1992 | Pristash et al. |
| 5,250,045 A | 10/1993 | Bohley |
| 5,353,786 A | 10/1994 | Wilk |
| 5,354,302 A | 10/1994 | Ko |
| 5,406,938 A | 4/1995 | Mersch et al. |
| 5,419,309 A | 5/1995 | Biehl |
| 5,419,313 A | 5/1995 | Lemke |
| 5,423,312 A | 6/1995 | Siegmund et al. |
| 5,516,227 A | 5/1996 | Kozak |
| 5,538,497 A | 7/1996 | Hori |
| 5,588,949 A | 12/1996 | Taylor et al. |
| 5,617,498 A | 4/1997 | Cawood |
| 5,709,459 A | 1/1998 | Gourgouliatos et al. |
| 5,745,632 A | 4/1998 | Dreyer |
| 5,785,648 A | 7/1998 | Min |
| 5,931,576 A | 8/1999 | Kreysar et al. |
| 5,947,958 A | 9/1999 | Woodard et al. |
| 6,185,356 B1 | 2/2001 | Parker et al. |
| 6,260,994 B1 | 7/2001 | Matsumoto |
| 6,293,910 B1 | 9/2001 | Yamakita et al. |
| 6,306,083 B1 | 10/2001 | Bonne et al. |
| 6,350,233 B1 | 2/2002 | Lubowski |
| 6,387,044 B1 * | 5/2002 | Tachibana ........ A61B 1/00135 600/114 |
| 6,449,006 B1 | 9/2002 | Shipp |
| 6,478,730 B1 | 11/2002 | Bala et al. |
| 6,504,985 B2 | 1/2003 | Parker et al. |
| 6,551,346 B2 | 4/2003 | Crossley |
| 6,561,973 B1 | 5/2003 | Bala |
| 6,621,973 B1 | 9/2003 | Hoffman |
| 6,679,838 B2 | 1/2004 | Bala |
| 6,814,699 B2 | 11/2004 | Ross et al. |
| 6,863,651 B2 | 3/2005 | Remijan et al. |
| 6,871,000 B1 | 3/2005 | Fukuba et al. |
| 6,945,933 B2 | 9/2005 | Branch et al. |
| 6,966,685 B2 | 11/2005 | Li et al. |
| 7,223,233 B2 | 5/2007 | Branch et al. |
| 7,306,559 B2 | 12/2007 | Williams |
| 7,510,524 B2 | 3/2009 | Vayser et al. |
| 7,901,353 B2 | 3/2011 | Vayser et al. |
| 8,162,824 B2 | 4/2012 | Vayser et al. |
| 8,708,896 B2 | 4/2014 | Vayser et al. |
| 9,005,115 B2 | 4/2015 | Vayser |
| 9,072,455 B2 | 7/2015 | Vayser et al. |
| 9,504,373 B2 | 11/2016 | Vayser et al. |
| 2002/0007111 A1 | 1/2002 | Deckert et al. |
| 2002/0055111 A1 | 5/2002 | Chen |
| 2002/0193664 A1 | 12/2002 | Ross et al. |
| 2003/0050534 A1 | 3/2003 | Kazakevich |
| 2003/0095417 A1 | 5/2003 | Keuper et al. |
| 2003/0095781 A1 | 5/2003 | Williams |
| 2003/0163030 A1 | 8/2003 | Arriaga |
| 2004/0032750 A1 | 2/2004 | Watts et al. |
| 2004/0141336 A1 | 7/2004 | West et al. |
| 2004/0143167 A1 | 7/2004 | Branch et al. |
| 2004/0143169 A1 | 7/2004 | Branch et al. |
| 2004/0252483 A1 | 12/2004 | Cheng |
| 2005/0147368 A1 | 7/2005 | Fukuba et al. |
| 2005/0277946 A1 | 12/2005 | Greenhalgh |
| 2005/0279354 A1 * | 12/2005 | Deutsch ................ A61B 1/07 128/200.24 |
| 2006/0069314 A1 | 3/2006 | Farr |
| 2006/0206007 A1 | 9/2006 | Bala |
| 2006/0211918 A1 | 9/2006 | Lieponis |
| 2006/0217597 A1 | 9/2006 | Vayser et al. |
| 2006/0224045 A1 | 10/2006 | Whipple et al. |

(56) References Cited

U.S. PATENT DOCUMENTS

| | | |
|---|---|---|
| 2006/0256575 A1 | 11/2006 | Vayser |
| 2006/0268570 A1 | 11/2006 | Vayser et al. |
| 2007/0078500 A1 | 4/2007 | Ryan et al. |
| 2007/0100210 A1* | 5/2007 | Selover ............ A61B 17/02 600/199 |
| 2007/0100211 A1* | 5/2007 | Selover ............ A61B 17/02 600/199 |
| 2007/0270653 A1 | 11/2007 | Vayser et al. |
| 2007/0274100 A1 | 11/2007 | Yang |
| 2007/0276191 A1 | 11/2007 | Selover et al. |
| 2008/0144330 A1 | 6/2008 | Buelow et al. |
| 2009/0036744 A1 | 2/2009 | Vayser et al. |
| 2009/0105546 A1 | 4/2009 | Hestad et al. |
| 2009/0182202 A1 | 7/2009 | Vayser et al. |
| 2009/0296205 A1 | 12/2009 | Ouchi |
| 2011/0021882 A1 | 1/2011 | Selover et al. |
| 2011/0058388 A1 | 3/2011 | Cassarly et al. |
| 2011/0201889 A1 | 8/2011 | Vayser et al. |
| 2012/0245413 A1 | 9/2012 | Vayser et al. |
| 2014/0213851 A1 | 7/2014 | Vayser et al. |
| 2015/0173596 A1 | 6/2015 | Vayser |
| 2017/0095310 A1 | 4/2017 | Vayser et al. |
| 2017/0095311 A1 | 4/2017 | Vayser et al. |
| 2017/0100023 A1 | 4/2017 | Vayser |
| 2017/0265734 A1 | 9/2017 | Vayser |

FOREIGN PATENT DOCUMENTS

| | | |
|---|---|---|
| EP | 0148034 A2 | 7/1985 |
| EP | 0148034 A3 | 11/1986 |
| GB | 1262214 A | 2/1972 |
| GB | 2078526 A | 1/1982 |
| WO | WO-9709937 A1 | 3/1997 |
| WO | WO-0013568 A1 | 3/2000 |
| WO | WO-0149164 A1 | 7/2001 |
| WO | WO-03051184 A1 | 6/2003 |

OTHER PUBLICATIONS

European search report dated Dec. 8, 2010 for EP 06749513.5.
International search report and written opinion dated May 4, 2007 for PCT/US2006/013029.
International search report and written opinion dated Sep. 22, 2008 for PCT/US2008/003779.
Notice of allowance dated Mar. 16, 2015 for U.S. Appl. No. 13/429,700.
Notice of allowance dated Aug. 1, 2016 for U.S. Appl. No. 14/229,528.
Notice of allowance dated Nov. 18, 2008 for U.S. Appl. No. 11/397,446.
Notice of allowance dated Dec. 2, 2014 for U.S. Appl. No. 12/188,055.
Notice of allowance dated Dec. 13, 2013 for U.S. Appl. No. 13/019,198.
Notice of allowance dated Dec. 16, 2010 for U.S. Appl. No. 11/715,247.
Notice of allowance dated Dec. 29, 2011 for U.S. Appl. No. 12/412,764.
Office action dated Mar. 9, 2012 for U.S. Appl. No. 12/188,055.
Office action dated Apr. 10, 2013 for U.S. Appl. No. 13/019,198.
Office action dated Apr. 19, 2007 for U.S. Appl. No. 11/397,446.
Office action dated Apr. 30, 2014 for U.S. Appl. No. 13/429,700.
Office action dated May 19, 2016 for U.S. Appl. No. 14/229,528.
Office action dated Jul. 7, 2011 for U.S. Appl. No. 12/412,764.
Office action dated Jul. 25, 2012 for U.S. Appl. No. 12/188,055.
Office action dated Aug. 1, 2014 for U.S. Appl. No. 12/188,055.
Office action dated Sep. 4, 2013 for U.S. Appl. No. 13/019,198.
Office action dated Oct. 6, 2015 for U.S. Appl. No. 14/229,528.
Office action dated Oct. 9, 2007 for U.S. Appl. No. 11/397,446.
Office action dated Nov. 4, 2016 for U.S. Appl. No. 14/635,996.
Office action dated Nov. 6, 2014 for U.S. Appl. No. 13/429,700.
European search report with written opinion dated Jul. 21, 2014 for EP14166681.
Office action dated Jan. 17, 2018 for U.S. Appl. No. 14/635,996.
Office action dated Feb. 8, 2018 for U.S. Appl. No. 15/384,710.
Office action dated May 25, 2017 for U.S. Appl. No. 14/635,996.
Office action dated Sep. 13, 2017 for U.S. Appl. No. 14/635,996.
"Office action dated Apr. 19, 2018 for U.S. Appl. No. 14/635,996."
"Office action dated Jul. 17, 2018 for U.S. Appl. No. 15/384,710."

* cited by examiner

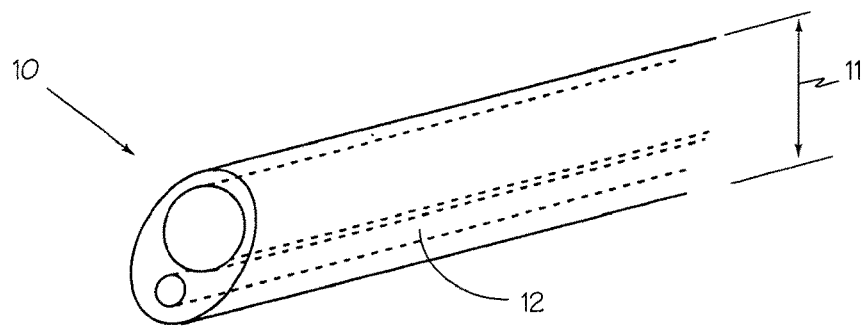
Fig. 1 (prior art)
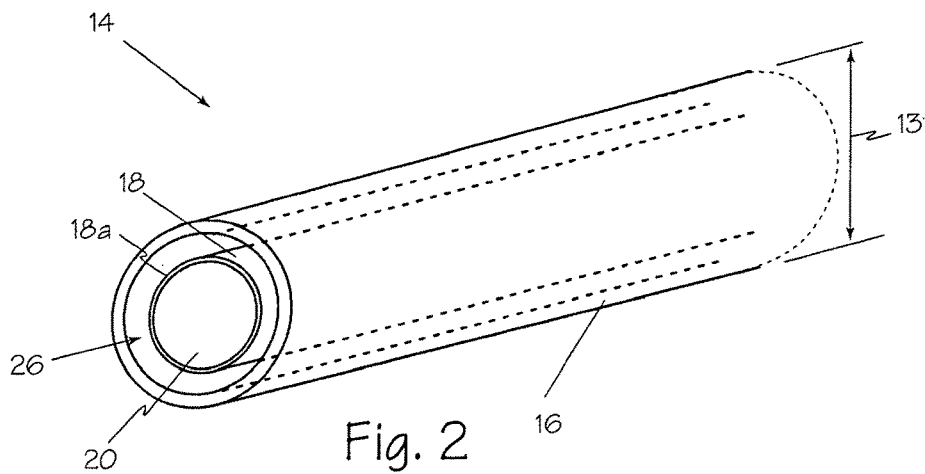
Fig. 2
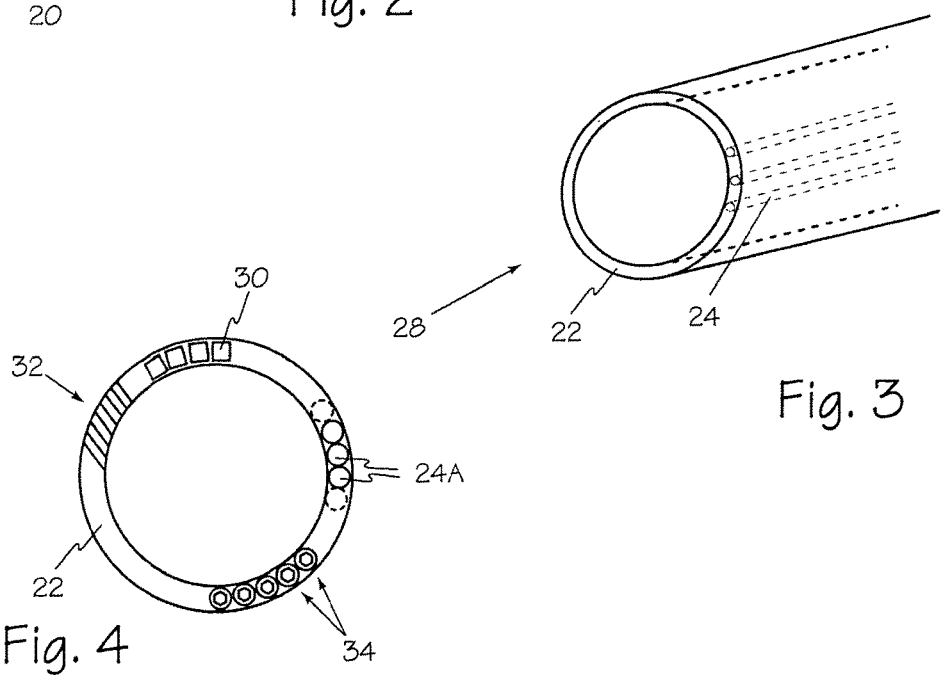
Fig. 3
Fig. 4

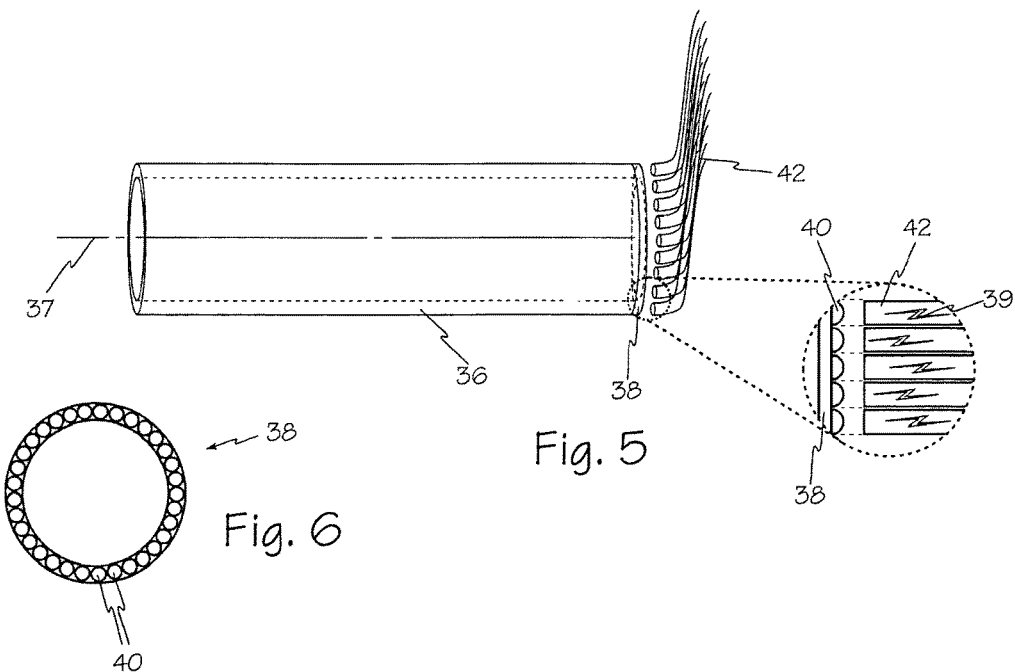
Fig. 5
Fig. 6
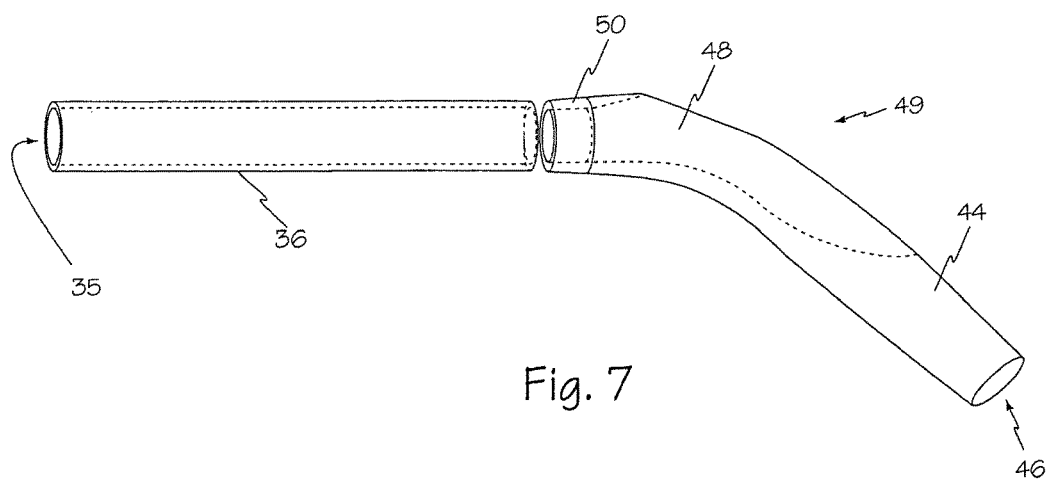
Fig. 7

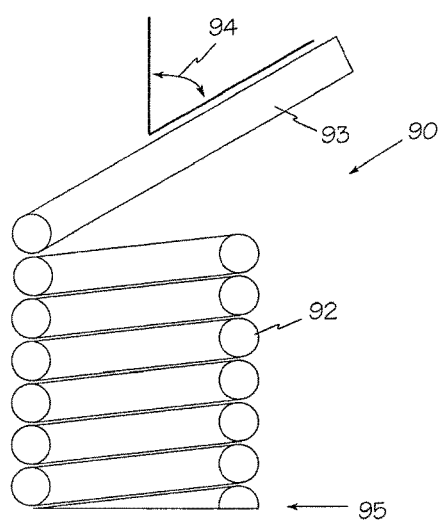
Fig. 14
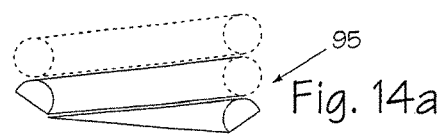
Fig. 14a
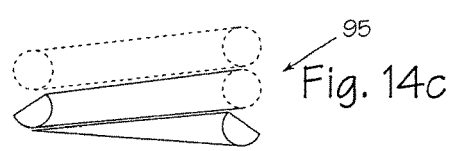
Fig. 14b
Fig. 14c
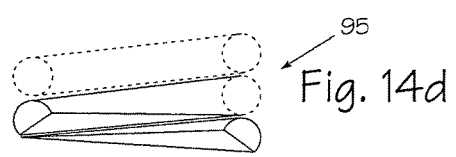
Fig. 14d
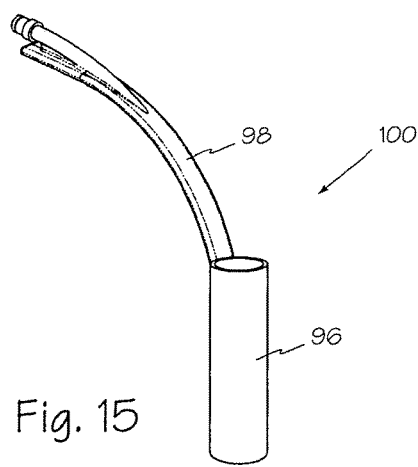
Fig. 15
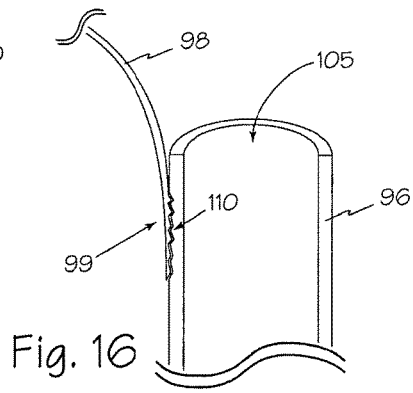
Fig. 16
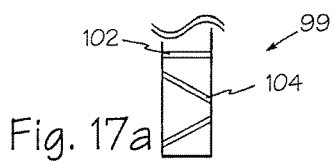
Fig. 17a
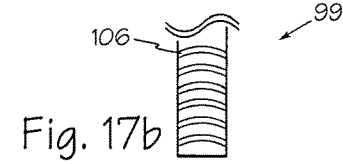
Fig. 17b
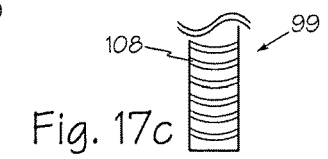
Fig. 17c

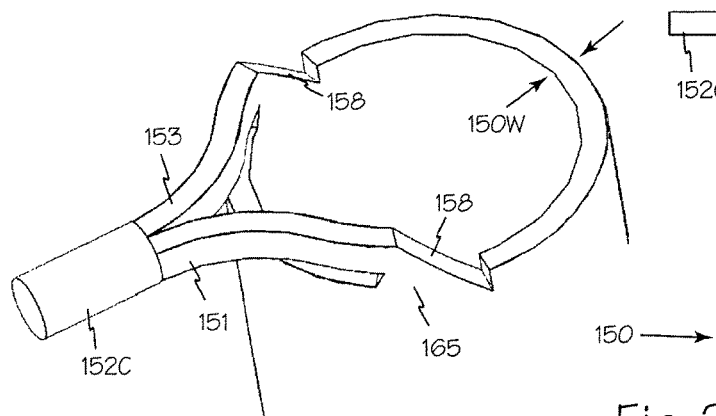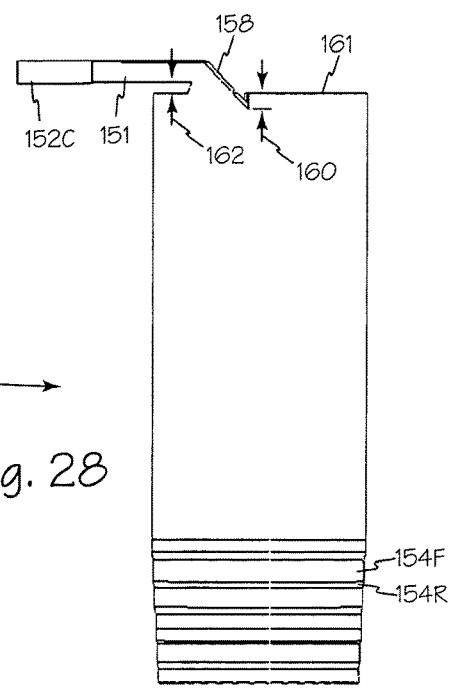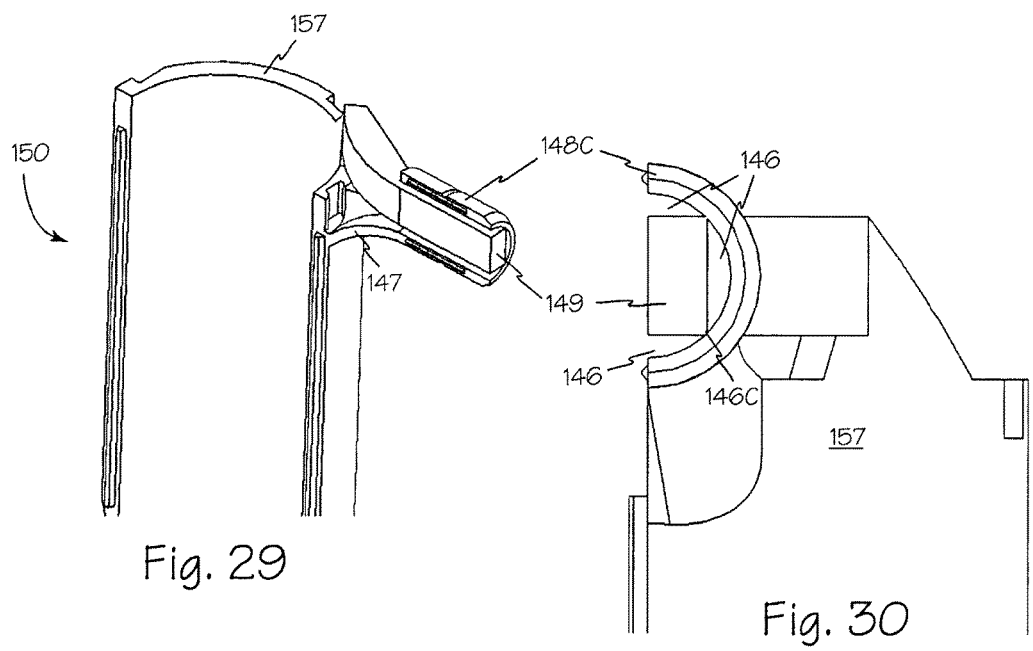
Fig. 27
Fig. 28
Fig. 29
Fig. 30

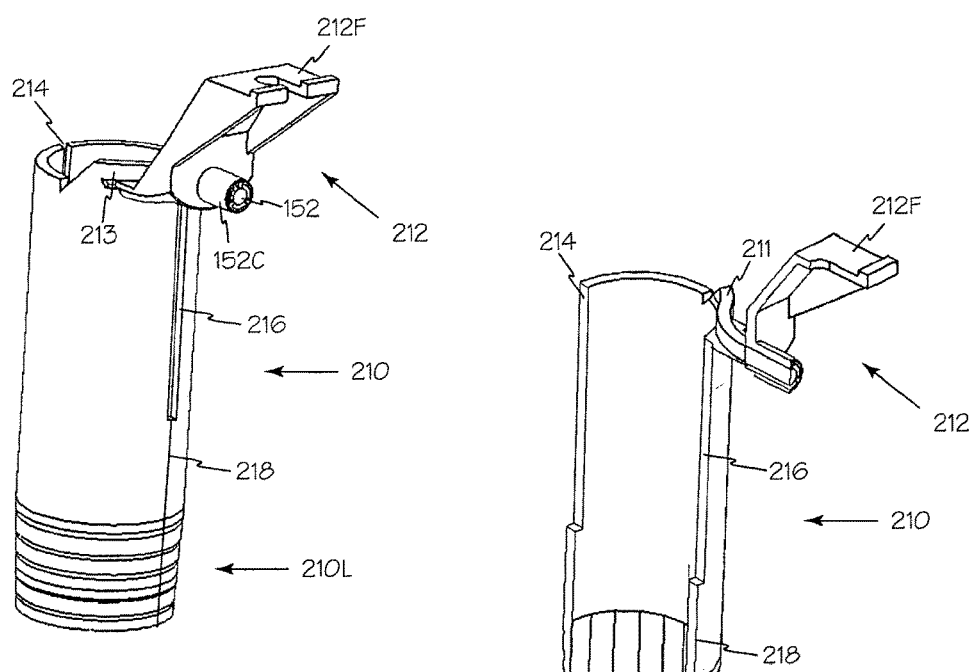
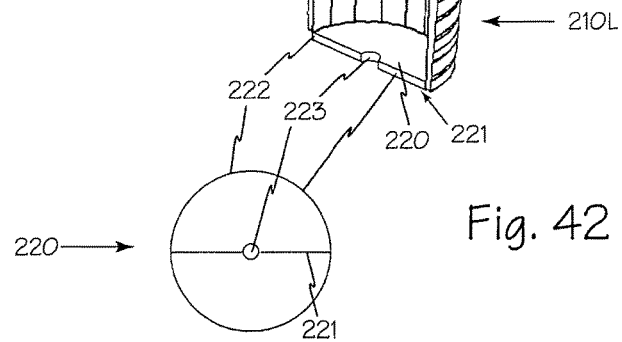
Fig. 41
Fig. 42

ILLUMINATED TELESCOPING CANNULA

CROSS-REFERENCE

The present application is a continuation of U.S. patent application Ser. No. 14/635,996, filed Mar. 2, 2015, which is a continuation of U.S. patent application Ser. No. 12/188,055 filed Aug. 7, 2008 now U.S. Pat. No. 9,005,115, which is a continuation in part of U.S. patent application Ser. No. 11/715,247 filed Mar. 6, 2007 now U.S. Pat. No. 7,901,353 which is a continuation in part of U.S. patent application Ser. No. 11/397,446 filed Apr. 3, 2006 now U.S. Pat. No. 7,510,524 which is a non-provisional of, and claims the benefit of U.S. Provisional Patent Application Nos. 60/724,717 filed Oct. 7, 2005, and 60/668,442 filed Apr. 4, 2005; the entire contents of each of which is incorporated herein by reference.

FIELD OF THE INVENTIONS

The present invention relates generally to the field of surgical illumination and more specifically to surgical cannulas providing illumination.

BACKGROUND OF THE INVENTION

Currently optical fiber illumination elements such as element 12 shown in FIG. 1 are used exclusively in medical illumination where small packaging is critical. Although the cost of raw glass or plastic fiber is relatively inexpensive, the cost of assembling the fiber into an endoscope tube or other surgical device may be high. Once the fiber is inserted, it generally must be glued and polished to a specific angle. Optical fiber is also extremely fragile and brittle. During the assembly process or in the field after many sterilization cycles, optical fiber and other conventional waveguide plastics may start to break down and degrade. Color change is also very common with fiber optics after many sterilization cycles. Since the fiber is integrated into a medical tool, any damage to the fiber optics also results in damage to the tool, thus causing an expensive overhaul. The relatively small size of the distal end of an illumination fiber also makes obscuration by blood or other material in a surgical site very likely and thus hinders to efficient surgery.

Another significant challenge in many conventionally illuminated procedures is cable management. There may be many cables typically present in the sterile field: camera cable, fiber optic cable, irrigation and suction, etc. Since the optical fiber cable has the largest diameter it typically is the heaviest cable. One of the challenges that face surgeons using illuminated tools is constant rotation of the illuminated tool to view different orientation angles. When an illuminated tool is rotated, the fiber optic cable is forced to rotate around with the tool, thus causing interference. These issues become even more important during arthroscopic surgery. Since the optical fiber cable is heavy, it will actually rotate the endoscope, often forcing the surgeon to keep one of their hands on the fiber optic cable to prevent unwanted spinning of the endoscope.

The illumination fiber also occupies space inside an illuminated tool, an endoscope or other surgical implement. By allocating space to optical fiber illumination, the diameter of optics may be limited to maintain the smallest overall tool size.

Typical coupling surfaces to a fiber optic cable are circular, mainly because the fiber cable itself is made with circularly bundled fibers. The problem is accounting for the various sizes of fiber bundles (e.g., 3.0 mm, 3.5 mm, 4 mm, 5 mm diameter bundles are common) to which a light conducting or light guiding device, also called a waveguide device, may be coupled in order to optimize coupling efficiency. Light that is not coupled from the fiber into the waveguide is lost light that cannot be used for illumination. In addition, this lost light may have infrared components that contribute to heating of the coupling connectors, which are typically metal in fiber optic cables. This heating may be significant enough to cause minor to major burns.

SUMMARY

An illuminated cannula port combines an illuminated waveguide cannula be formed to have thin walls with a thin walled cannula sleeve of metal or other suitable material to achieve tissue retraction to create a surgical site and deliver illumination to the surgical site from the bottom of the waveguide cannula within the cannula sleeve. The cannula sleeve may be longer than the waveguide cannula. The waveguide cannula and the cannula sleeve are separate pieces and are free to move relative to each other to provide a wide range of cannula port lengths using the relative telescoping movement between the waveguide cannula and the cannula sleeve.

The waveguide sleeve may have many different geometries as, for example, a right circular cylinder, or the bottom edge may have any suitable angle relative to the axis of the sleeve bore to prevent tissue creep. The ability to move the waveguide cannula and the cannula sleeve relative to each other enables a surgeon to move the sleeve to accommodate tissue requirements without the need to move the illumination cable and the waveguide cannula. Similarly, if the surgeons light needs vary during the surgery, it is possible to move the illumination cable and the waveguide cannula without changing the position of the cannula sleeve.

An illuminated waveguide cannula as a single unit that may be molded into custom shapes and or made single use disposable. If the waveguide is single use and sold sterile, it will be brand new for every application, so if any damage occurs during a procedure, the waveguide may be easily replaced and may be discarded after a procedure.

A surgical illumination system according to the present disclosure may include a generally cylindrical light waveguide having a bore sized to accommodate one or more surgical instruments, an illumination source, an illumination conduit for conducting illumination energy from the illumination source, and an adapter ring for engaging the illumination conduit and coupling illumination energy from the illumination conduit to the light waveguide, the adapter ring permitting relative movement between the illumination conduit and the light waveguide.

A surgical illumination system may also include an illumination source, a generally cylindrical light waveguide having a distal end and a proximal end and a bore sized to accommodate one or more instruments or tools extending from the proximal end through the distal end, the waveguide conducting illumination energy from the proximal end to the distal end and projecting the illumination energy from the distal end, and an illumination conduit for conducting illumination energy from the illumination source to the proximal end of the light waveguide. A secondary cannula may be combined with the waveguide cannula to provide mechanical retraction and enable the waveguide cannula to be rotated relative to the secondary cannula as well as providing adjustable depth.

Since multiple ports are commonly used in endoscopy and, typically, a cannula or trocar is placed at each port, one or more of the port cannulas or port trocars could be a waveguide designed to spread light in the desired direction in one embodiment. Use of illuminated cannula or waveguides enables the light to shine circumferentially from the port cannula or can make it shine in a particular direction from the port cannula. The intensity of light may be adjusted circumferentially to maximize shadow creation, for example, by concentrating extraction structures along a particular arc of the port cannula and using less concentrated extraction structures along another arc and having no structures on the remaining arc, or using less concentrated structures along the remaining arc. Directionality can be simply controlled by rotating the port cannula to shine the higher intensity light to maximize shadowing. Another option is to put a rotatable reflector or director partially around the waveguide or otherwise adjustably engaged with the waveguide. Light from the waveguide, e.g., a waveguide producing light circumferentially, is reflected and or directed by this reflector/director, e.g., a mirror-polished metal or plastic component or a component with a reflective film, in a particular direction. The user merely rotates the reflector/director rather than rotating the waveguide itself, which may be cumbersome with a fiber optic cable attached to the waveguide.

In another configuration, a small "chandelier" waveguide may be placed vertically or at a particular angular orientation to the interior work surface using a very small puncture wound that is separate from the main surgical ports. This chandelier waveguide may provide circumferential or directed light and may include a secondary reflector/director as described above. The waveguide may be protected during insertion by using an introducer that goes over the waveguide, said introducer having a sufficiently sharp point to create the wound or the surgeon creates a small wound for the introducer to go into. Once the introducer and waveguide are in place, the introducer is slid back up the waveguide to expose the light extraction structures. This can be accomplished, for example, by creating the point of the introducer out of a set of radial splines that are curved and shaped to form a point or blunt tip for insertion into the wound. Once in place, the introducer is pulled out and the splines spread out over the waveguide. Alternatively, the introducer and reflector/director are the same component and remain in place after insertion into the wound to provide directional light control. Output from the chandelier waveguide may be combined with light from instrument ports that are also designed as waveguide devices, or themselves may use the waveguide ports.

The surgical illumination systems may also be distributed pre-sterilized along with one or more generally used instruments and accessory parts that may be used by most surgeons. Thus a sterile waveguide may be supplied for a surgery and discarded after use minimizing parts to be reused, inventoried and resterilized.

These and other features and advantages will become further apparent from the detailed description and accompanying figures that follow. In the figures and description, numerals indicate the various features of the disclosure, like numerals referring to like features throughout both the drawings and the description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a perspective view of the distal end of a conventional endoscope.

FIG. 2 is a perspective view of the distal end of an endoscope with an optical waveguide sheath according to the present disclosure.

FIG. 3 is a perspective view of the distal end of an optical waveguide sheath according to the present disclosure.

FIG. 4 is an end view of the distal end of an optical waveguide sheath according to the present disclosure.

FIG. 5 is a side view of an optical waveguide sheath coupling to fiber optic elements.

FIG. 6 is an end view of the fiber optic coupling lens array of FIG. 5.

FIG. 7 is a side view of an optical waveguide sheath with a light-coupling adapter according to the present disclosure.

FIG. 14 is a cutaway view of an alternate optical waveguide.

FIGS. 14*a*-14*d* are cutaway views of alternate distal ends of the optical waveguide of FIG. 14.

FIG. 15 is a perspective view of an optical waveguide with an alternate light coupling.

FIG. 16 is a cutaway view of the proximal end of the optical waveguide of FIG. 15.

FIGS. 17*a*-17*c* are front views alternate distal ends of the light coupling of FIG. 15.

FIG. 27 is a perspective view of the optical waveguide of FIG. 25 with the clamp assembly removed for clarity.

FIG. 28 is a side view of the optical waveguide of FIG. 27.

FIG. 29 is a cutaway perspective view of an optical waveguide with the clamp assembly removed for clarity.

FIG. 30 is a close up front view of the input connector of FIG. 29.

FIG. 41 is a perspective view of a separable waveguide.

FIG. 42 is a cutaway view of the optical waveguide of FIG. 41.

DETAILED DESCRIPTION OF THE INVENTION

Figure 8:
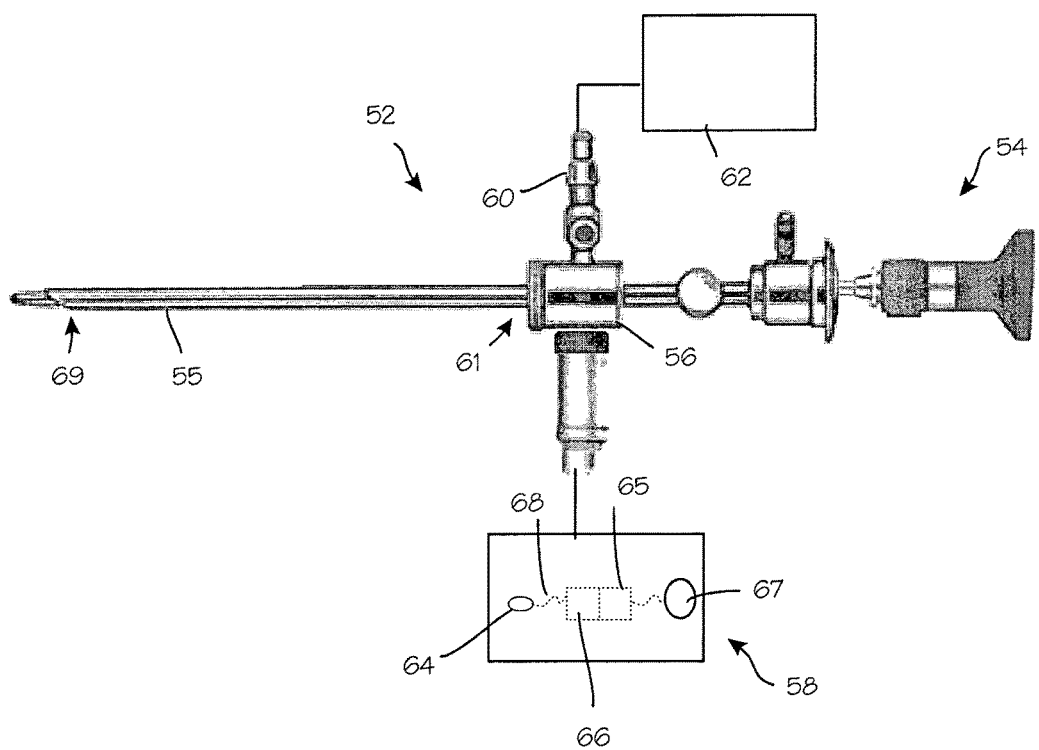
FIG. 8 is a side view of an optical waveguide illumination system with a high-resolution arthroscope disposed therein.

The following disclosure generally refers to an optical waveguide and associated elements for conduction of light. This discussion is for example and the following disclosure may also be suitable for any electromagnetic radiation. The cross-sections illustrated are generally circular and may also adopt any suitable geometry.

Referring now to FIG. 2, optical waveguide system 14 may accommodate any suitable surgical instrument such as for example, a drill, burr or endoscope 18 which is encased, enclosed or otherwise surrounded by optical waveguide sheath 16. An optical waveguide sheath according to the present disclosure is a generally annular or cylindrical shaped structure and may be manufactured separately and may be a single use device. In the event of a failure of an optical waveguide such as optical waveguide sheath 16, a replacement may be introduced immediately. One or more flow paths such as flow path 26 may be created between endoscope 18 and optical waveguide sheath 16. Flow path 26 may be used for any suitable service such as suction, irrigation, ventilation or the introduction of other tools or devices. A waveguide sheath may be subjected to forces during use, such as a prying force, that may weaken or break it. Structural elements such as gussets or ribs may be added to waveguide sheath 16 in the bore between the sheath and endoscope 18 that serve to strengthen waveguide sheath 16. A film may be added to the outside of waveguide sheath 16 to secure pieces that may become broken during use to prevent the broken pieces from dropping into the surgical work space. Said film may serve an optical function as well, e.g., enhancing total internal reflection within the wall of waveguide sheath 16.

Surgical devices such as endoscope 18 may be made without an illumination element and thus aperture 20 may be increased without increasing overall dimension 13 compared to dimension 11 of the device of FIG. 1. Wall 18A of endoscope 18 may also be perform as optical waveguide to improve illumination and may provide an alternate light path to enable illumination of different characteristics.

Referring now to FIG. 3, waveguide sheath 28 may be a single generally uniform element, it may be composed of two or more distinct illumination pathways forming an apparently singular conduit, or it may be composed of one or more parallel light conducting elements such as light path element 24 or light path element 92 of FIG. 14. Moving the illumination element from conventional endoscopes to a separate device such as a light conduit such as waveguide sheath 28 permits illumination surface 22 to be larger than many conventional illumination elements. Surrounding an apparatus such as an endoscope with the optical waveguide may provide generally uniform illumination for any orientation of the endoscope or other device.

Referring now to FIG. 4, illumination surface 22 may adopt any suitable configuration to provide illumination. For example facets such as facets 30 may direct light energy in any selected direction and may be coated or otherwise treated to introduce filtering for frequency and or polarization. Microstructures such as microstructures 32 may be used to achieve directed light energy, filtering or other. One or more lens structures may be coupled to illumination surface 22, or they may be formed in or on illumination surface such as lenses 34. Alternatively, these elements may also be combined.

Using separate light conducting elements such as light path elements 24 may permit selective illumination through a waveguide sheath as well as provide multiple illumination paths for illumination having different characteristics such as polarization, wavelength or intensity. Each light path element may include microstructures, facets, lenses or other suitable treatment on distal face 24A.

In FIGS. 5 and 6 coupling ring 38 is provided to couple light from fibers 42 into optical waveguide 36. Coupling ring 38 permits rotation of optical waveguide 36 about bore centerline 37 without rotating fibers 42. Coupling ring 38 may be made reusable since it includes the expensive optical fibers whereas optical waveguide 36 may be made disposable, e.g., as an inexpensive plastic injection molded part using a suitable optical material such as acrylic or polycarbonate. Coupling ring 38 may also include any suitable light coupling structure such as coupling lenses such as lenses 40, each lens coupling light energy 39 from a fiber 42 into optical waveguide 36. The lenses or suitable microstructure may be spherical, cylindrical or aspherical or non-symmetrical depending on the light source. In the case of fiber optics, a spherical lens may be used to match the numerical apertures (acceptance angle) of the fiber optic and the optical waveguide. Because a specific cone angle of light exits a fiber optic cable, a matching acceptance angle should be used for the coupling ring.

Referring now to FIG. 7, light coupling adapter 44 may be used to couple light energy in through face 46 and directs the light energy around access channel 48 and through adapter ring 50 into optical waveguide 36. Access port 49 and access channel 48 provide access to bore 35 for any suitable surgical tool, apparatus or device. Adapter ring 50 engages waveguide 36 while permitting relative motion of waveguide 36 relative to light coupling adapter 44. Alternatively, coupling adapter 44, adapter ring 50 and optical waveguide 36 may be contiguous with no relative motion permitted. Coupling ring 50 may also be an element of waveguide 36 as well as an element of light coupling adapter 44.

FIG. 8 illustrates arthroscopic illumination system 52 with a high-resolution arthroscope 54 disposed therein. The arthroscopic illumination system comprises a cannula sheath 55 adapted to provide structure-guided illumination, a hub 56 and an illumination source 58. The hub may contain one or more valves 60 and be placed in fluid communication with a vacuum and/or irrigation source 62. The cannula sheath 55 comprises a biocompatible sterilizable polymer that functions as a waveguide. The polymer may be transparent or semi-transparent and may incorporate facets, prisms, microstructures or other suitable characteristics.

An illumination source is operably coupled to the hub 56 and placed in optical communication with the cannula sheath 55. The illumination source comprises one or more LEDs 64 (light emitting diodes), a power source 66, a conductor 68 electrically connecting the power source and the LED, an LED control circuit 65 and switch 67. The LED is preferably a white-light LED, which provides a bright, white light. The power source may be provided in any form such as a power outlet or a lithium ion polymer battery. When the illumination source is illuminated, light from the illumination source propagates through the cannula sheath by means of total internal reflection, illuminating the distal end 69 of the cannula sheath. Light is not emitted, nor does it leak out of the outer diameter surface of the sleeve until the light reaches designated extraction structures. The outer surfaces of the sleeve may be provided with metallic or other suitable coating to help prevent light leakage while assisting with total internal reflection. The distal end of the sleeve may be provided with a microstructure, optical component or a diffuse finish. Based on the desired optical output, a molded component or custom finish may be applied to filter or shape the light exiting the sheath.

Alternatively, the illumination source may comprise a conventional fiber light cable operably connected to the hub. The illumination source may be placed in optical communication with the sheath through optical coupling lenses disposed on the proximal end of sleeve 61 within hub 56.

Figure 9:
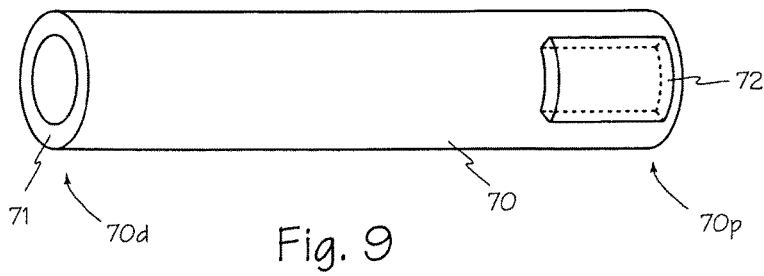
FIG. 9 is a side perspective view of an alternate optical waveguide light coupling technique.
Figure 10:
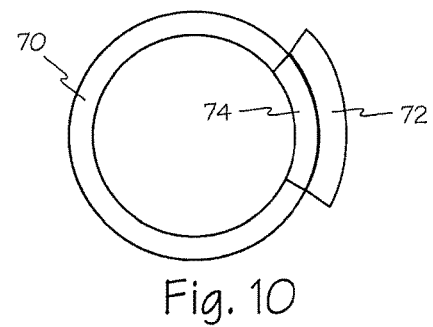
FIG. 10 is an end view of the optical waveguide of FIG. 9.

Referring now to FIGS. 9 and 10, light energy from LED array 72 may be coupled into optical waveguide 70 using reflective and or refractive optical assembly 74 in proximal end 70p such that light energy is projected from illumination surface 71 on distal end 70d.

Figure 11A:
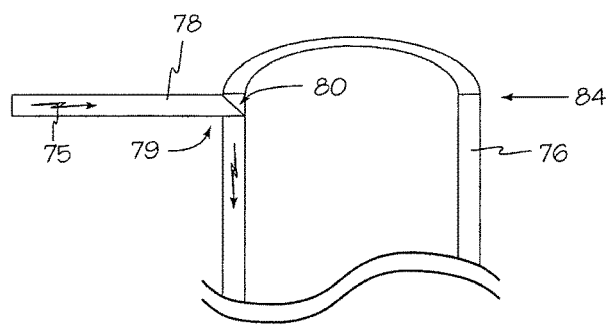
FIG. 11A is a cutaway view of the proximal end of an optical waveguide with another alternate light coupling.
Figure 11B:
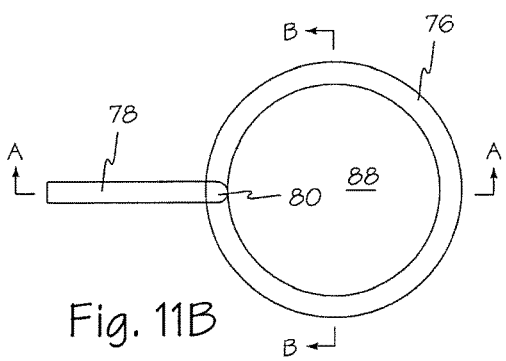
FIG. 11B is an end view of an optical waveguide of FIG. 11A.
Figure 11C:
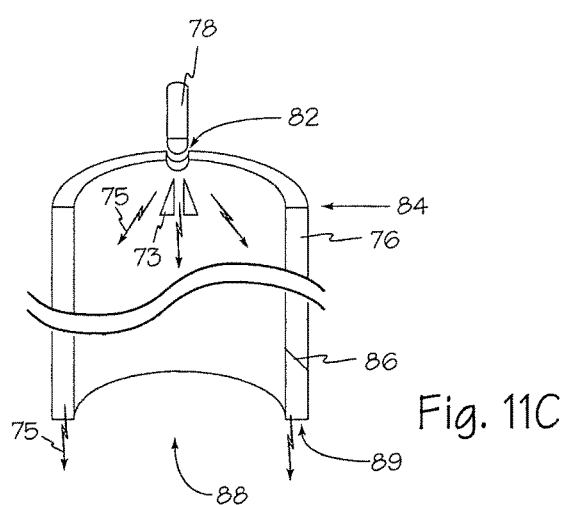
FIG. 11C is a cutaway view of the proximal end of the optical waveguide of FIG. 11B taken along B-B.

FIGS. 11A, 11B and 11C illustrate an alternate light coupling into optical waveguide 76. Light 75 may be provided through any suitable conduit such as plastic rod 78. Light conduit 78 may be formed, cut or otherwise shaped at engagement end 79 to reflect light 75 at any suitable angle relative to light conduit 78. Surface 80 may include any suitable treatment, coating or microstructure to reflect a suitable amount of light 75 at a suitable angle relative to light conduit 78.

A notch, groove or other suitable indentation such as u-shaped notch 82 may be provided in proximal end 84 of an optical waveguide to engage a light conduit such as plastic rod 78. The shape of notch 82 may be selected to optimize light coupling between the light conduit and the optical waveguide. One or more structures such as reflectors 73 and or facet 86 may be included in any suitable location of an optical waveguide to spread the input light throughout the waveguide and or reflect light into bore 88 or out of the optical waveguide into areas surrounding the waveguide. Light generally exits optical waveguide through illumination surface 89. One or more light splitting prisms such as prisms 73 may be added to a waveguide or to a coupling such as coupling 81 of FIG. 12 to direct the light around the circumference of waveguide 76. Two or more such prisms may be placed in spaced relation to each other to allow some light to spread straight down through the gap between prisms while light hitting the prisms is directed around the circumference.

Figure 12:
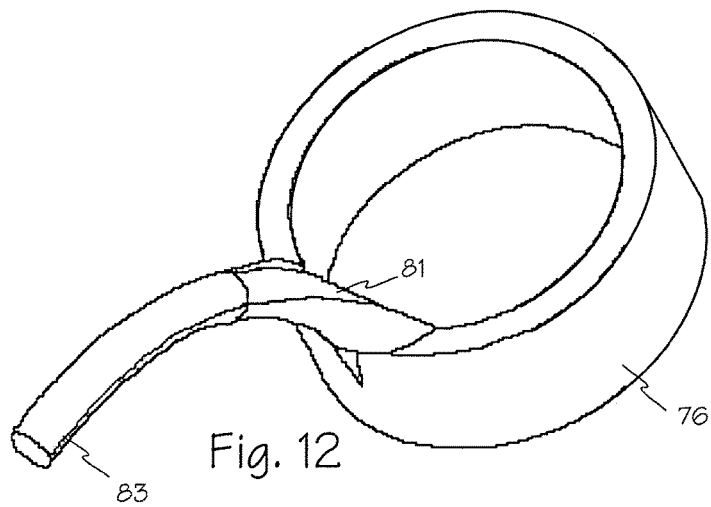
FIG. 12 is a perspective view of an optical waveguide with yet another input light coupling.

Referring now to FIG. 12, optical waveguide 76 may include an alternate light coupling apparatus such as coupling 81. Coupling 81 may provide mechanical support and optical conduit between optical input 83 and waveguide 76.

Figure 13:
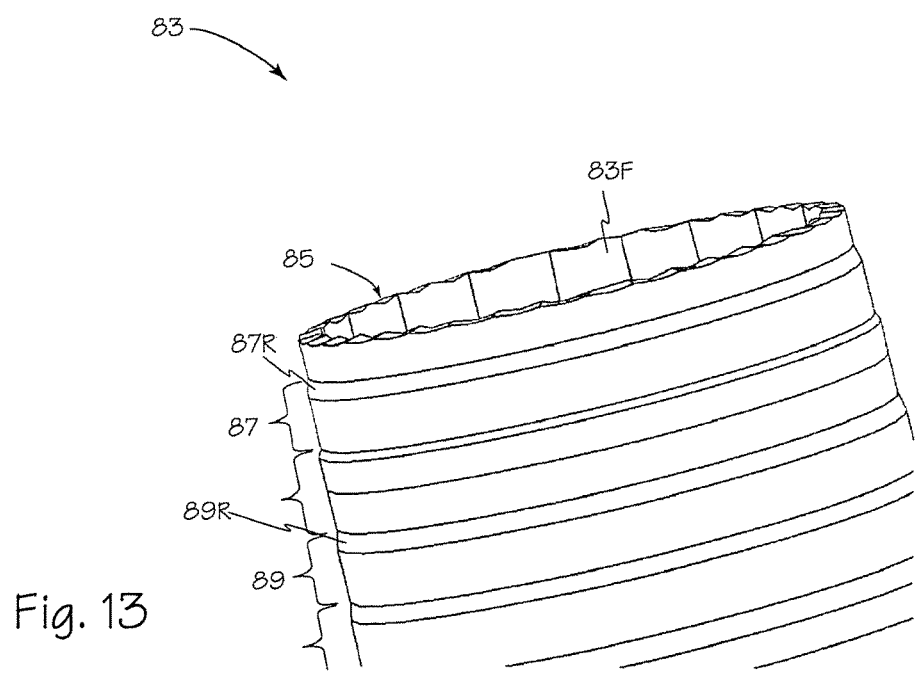
FIG. 13 is an enlarged perspective view of the distal end of an optical waveguide.

Distal end 83 as shown in FIG. 13 includes one of more vertical facets such as facet 83F within the distal end to disrupt the light spiraling within the waveguide. Also shown are structures such as structure 85 on the end face of the cannula which serve to direct light as it exits the end face. Shown are convex lenses, but concave lenses or other optical structures (e.g., stamped foil diffuser) may be employed depending on the desired light control. Stepped facets such as facets 87 and 89 are shown on the outside tube wall. The "riser" section, risers 87R and 89R respectively, of the stepped facet is angled to cause the light to exit and as a result the waveguide slides against tissue without damaging the tissue. The angle is generally obtuse relative to the adjacent distal surface. Steps may be uniform or non-uniform as shown (second step from end is smaller than the first or third step) depending on the light directional control desired. The steps may be designed to direct light substantially inwards and or toward the bottom of the tube or some distance from the bottom of the tube, or they may be designed to direct light toward the outside of the tube, or any suitable combination. The facets such as facets 87 and 89 may be each designed to direct light at different angles away from the waveguide and or may be designed to provide different beam spreads from each facet, e.g., by using different micro-structure diffusers on each facet face.

Facets may be used on the inside surface of the waveguide, but if waveguide material is removed to form the facets, the shape of the waveguide may be changed to maintain the internal diameter of the bore generally constant to prevent formation of a gap is between the waveguide and a dilator tube used to insert the waveguide into the body. Said gap may trap tissue, thereby damaging it during insertion into the body or causing the waveguide to be difficult to insert. Thus the outer wall of the waveguide may appear to narrow to close this gap and prevent the problems noted.

Alternatively, optical waveguide 90 as illustrated in FIGS. 14 and 14a-14d may be formed using one or more solid light guides such as light path element or rod 92 and forming the one or more rods into a spring like spiral. Input 93 may be formed at any suitable angle 94 with an optimal angle between 45° and 90°. Distal end 95 may be cut or formed to have any suitable configuration to reflect or emit light in any suitable direction or directions as illustrated in FIGS. 14 and 14a-14d for example. A spiral waveguide may be mechanically flexible, much as a spring is flexible. The spiral waveguide may be part of an assembly that includes rigid or semi-rigid tubular waveguides interconnected by spiral waveguides. Either or both of the tubular and spiral waveguides may have light extraction structures.

Surgical illumination system 100 may include optical waveguide 96 and light adapter 98. Distal end 99 of light adapter 98 may have any suitable shape as illustrated in FIGS. 17a-17c. Lenses or other optical structures such as lenses 102, 104, 106 and 108 may have any suitable shape or orientation to optimize light coupling, extraction or output. Different lenses may also be combined on a light adapter as in FIG. 17a. A complimentary surface 110 may be produced in optical waveguide 96 to achieve selected light transfer or coupling.

Alternatively, light adapter 98 may extend through optical waveguide 96 such that lenses such as lenses 102, 104, 106 and or 108 directly illuminate bore 105 and or the surgical site.

An optical waveguide may also be used with any suitable end cap engaging the distal end of the optical waveguide. The end cap may or may not be used to modify or reflect the illumination energy. Similarly, shims may be used within the optical waveguide to orient any tool or tools within the waveguide and the shims may or may not conduct or modify the illumination energy.

Figure 18:
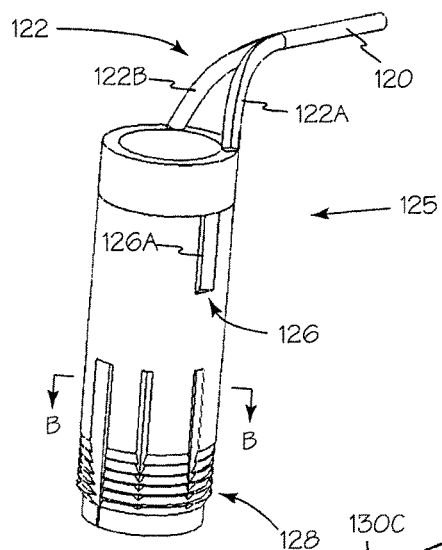
FIG. 18 is a perspective view of an optical waveguide with a split input coupling.
Figure 19:
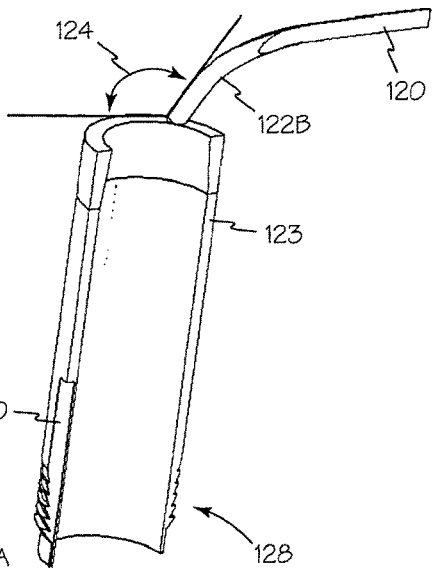
FIG. 19 is cutaway view of the optical waveguide of FIG. 18.
Figure 20:
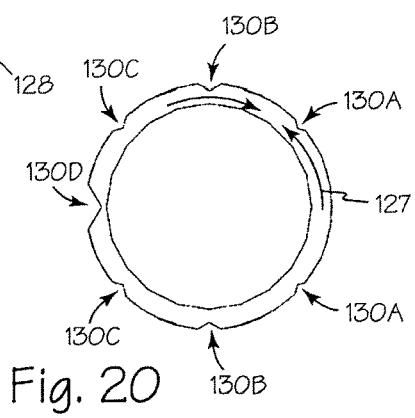
FIG. 20 is and cross-section of the optical waveguide of FIG. 18 taken along B-B.

Referring now to FIGS. 18, 19 and 20, applied light energy may be bifurcated to send light into wall 123 of tube 125. Light input 120 may be split in input coupling 122. The input coupling may be a solid plastic or may consist of a bundle of optical fibers. Optical fibers may be preferred because it is then possible to combine the waveguide and the optical fiber bundle, typically a separate cable used to conduct light from a light source to the waveguide, as one single device thereby eliminating the need for the user to maintain separate fiber optic cables. The optical fiber input 120 may also be provided as a short "pigtail" section, typically less than two feet long, to which a standard optical fiber cable attaches. The optical fibers may be insert molded with the waveguide or may be glued into corresponding holes in the waveguide using a suitable index-matching adhesive. The holes may include a collar section or other technique to provide strain relief. Typically, fiber bundles are made round. In a preferred embodiment, the optical fibers at the end to be coupled into the waveguide are shaped to match the waveguide, which may not be circular. For example, the section of the tube waveguide into which the optical fibers go may be approximated as a rectangular profile. Shaping the optical fibers into a matching rectangular profile simplifies the resulting optical design because the light dispersion from the optical fibers already conforms to the shape of the waveguide.

The bifurcated ends 122A and 122B of input 122 preferably enter tube wall 123 at an angle 124 to start directing light around the tube wall. Alternatively, the bifurcated ends 122A and 122B may each enter tube wall 123 at different angles to further control light distribution. The bifurcated ends may enter the tube wall orthogonally, but this may require a prism structure in the wall placed between the input and the output with the apex of the prism pointed at the input. The prism structure directs the light around the tube wall. A vertical prism structure, prism 126 is shown with apex 126A of the prism pointed in toward the center of the tube. Prism structure 126 may direct a portion of the input light back underneath the inputs and contributes to directing light all the way around the tube wall. The position, angle and size of this prism relative to the input bifurcated end determines how much light continues in the tube wall in its primary direction and how much light is reflected in the opposite direction in the tube wall.

Additional vertical prism structures or light disruption structures may be placed toward the bottom of the tube on the outside tube wall as shown in FIGS. 18, 19 and 20. One or more light extraction structures 128, shown as circumferential grooves cut into the outside wall of the tube, may also be included to optimize the illumination provided below waveguide 125. Light 127 traveling circumferentially in the tube wall will not strike the light extraction structures 128 with sufficient angle to exit waveguide 125. Thus, vertical prisms or light disruption structures such as disruption prisms 130A, 130B, 130C and 130D may be necessary to redirect the light so that the light rays will strike the light extraction structures and exit the tube wall to provide illumination. As shown in FIG. 20, vertical prism structures such as 130A and 130B have different depths around the circumference in order to affect substantially all of the light rays traveling circumferentially in the tube wall. Vertical prisms of constant depth would not affect substantially all of the light rays.

FIG. 19 also illustrates how a half-tube may be formed to provide illumination. At least one half-tube illuminator may be attached to the end of at least one arm of a frame, such as that used in Adson, Williams or McCulloch retractors. Such frames typically include two arms, but some frames have more than two arms. The arms of the frame are then moved apart to create a surgical workspace, with the at least one half-tube illuminator providing illumination of said space. One or more half-tube illuminators may also be provided with an extension that preferably is in contact with the opposite half tube and that serves to prevent tissue from filling in the gap created when the half tubes are separated. Tissue may enter this gap and interfere with surgery, so the extension helps reduce that issue. The extension is preferably thin and flexible, for example, a thin section of plastic molded or otherwise secured to the waveguide or a thin section of metal or other suitable material attached to the waveguide.

Figure 21:
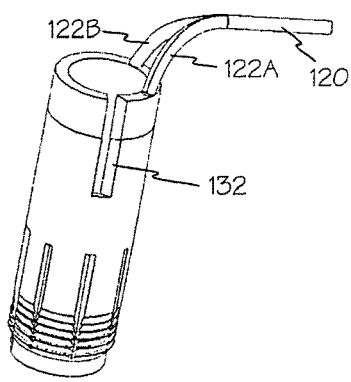
FIG. 21 is a perspective view of an alternate optical waveguide with a split input coupling.
Figure 22:
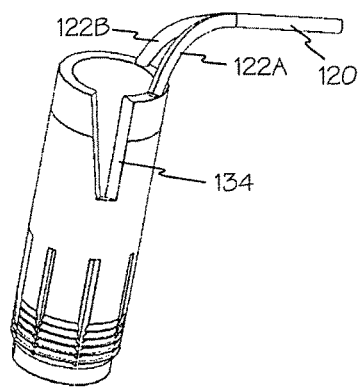
FIG. 22 is a perspective view of another alternate optical waveguide with a split input coupling.

FIGS. 21 and 22 illustrate alternative configurations of an illumination waveguide. Proximal reflecting structures such as proximal structure 132 and proximal structure 134 may provide more complete control of the light within the waveguide with an associated weakening of the structure.

Figure 23:
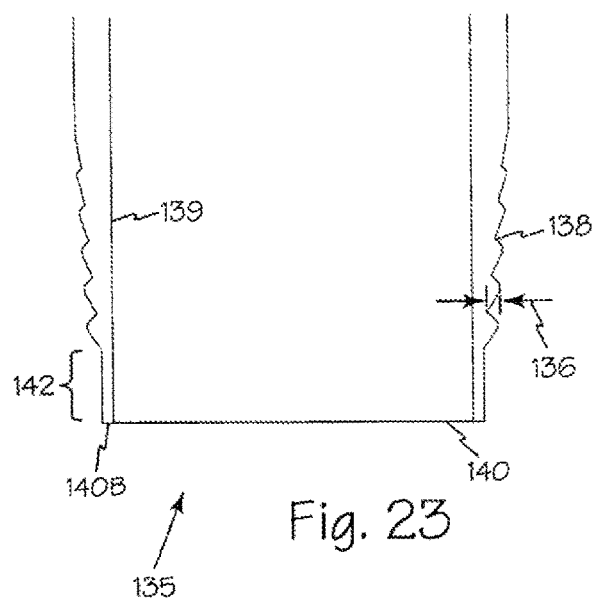
FIG. 23 is a cross section of the distal end of an optical waveguide.
Figure 24:
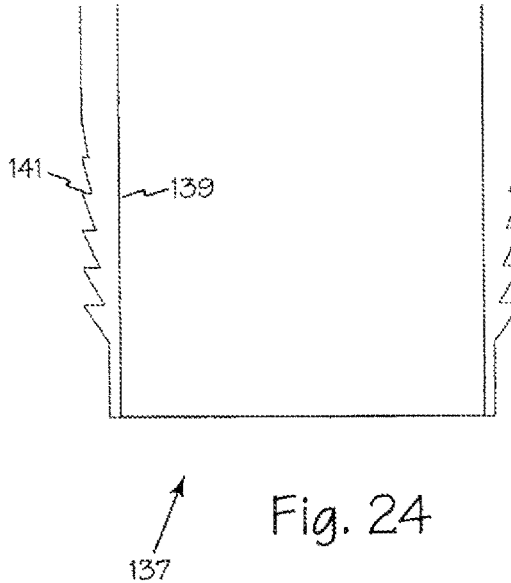
FIG. 24 is a cross-section of the distal end of an alternate optical waveguide.

Referring now to FIGS. 23 and 24, cross-sections 135 and 137 illustrate additional alternate light extraction structures of the distal end of an illumination waveguide. As shown with respect to FIG. 13 above, depth 136 of light extraction structures such as structures 138 and 141 increases relative to the distance from the light input in order to extract most of the light and send the light out the inner tube wall 139 toward the bottom of the tube or distal end 140 and for some distance beyond the distal end. The light that remains in the tube wall below the extraction structures exits the bottom edge 140B, which may be flat or may have additional optical structures, e.g., a curved lens or a pattern of light diffusing structures such as structures 85 of FIG. 13. In FIG. 23, the distal 510 mm of the tube wall, window 142, have no structures to enable this surface to operate as a window to the surrounding tissues to improve visualization of the surgical space.

It has been demonstrated that a clear waveguide cannula provides improved visualization of the entire surgical workspace because the surgeon can see the layers of tissue through the walls, thereby enhancing the surgeon's sense of depth and position, which are difficult to determine in an opaque cannula. Light exiting the side walls at the areas of tissue contact, due to changes in total internal reflection at these contact areas, serves to illuminate these tissues making them more visible than if a non-illuminated, non-waveguide clear plastic cannula is used. Alternatively, extraction structures 138 or 141 may extend all the way down to bottom edge 140B.

Referring now to FIGS. 25-28, light input connector 152C surrounds light input cylinder 152 which may be divided into multiple input arms such as arms 151 and 153 that then direct light into illumination waveguide 150. Input arms 151 and 153 may assume any suitable shape and cross-sections depending on the optical design goals, such as the multi-radius arms with rectangular cross-section shown or straight sections (no radius) or angle rotators, etc. Also shown is a clamp flange holder 159 that serves to support input connector 152C and arms as well as providing a standard light connector 152C over input cylinder 152 (e.g., an ACMI or WOLF connector) and a flange 159F at the top for attaching a clamp used to hold the entire structure in place once it is positioned relative to a surgical site in a body. A shelf, glare shield 159s, or other similar light blocking structures may be added to the holder, extending over the input arms and or the upper tube edge as needed to help block any light that may escape these structures that might shine up into the user's eyes. Circumferential light extraction structures 154 are shown at the bottom, distal end 156, of the tube. In the section view of FIG. 26, vertical light disruption structures or facets 83F are shown on the inside wall of the tube.

Figure 25:
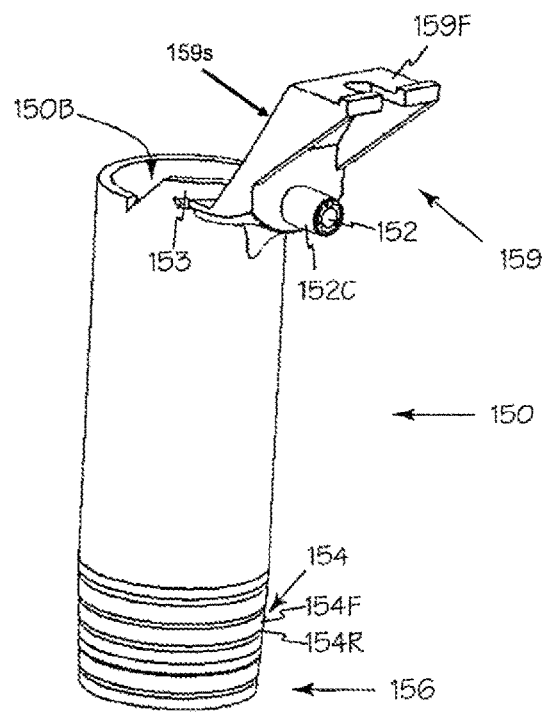
FIG. 25 is a perspective view of an alternate optical waveguide with a reinforced and shielded split input coupling.

Illuminated cannula 150 of FIG. 25 includes clamp adapter 159F that also support light coupling 152C for introducing light energy into cannula 150. The relative orientation of the clamp adapter and the light coupling as shown enables the clamp adapter to operate as a shield to prevent any misdirected light shining into the eyes of anyone looking into bore 150B of the cannula, but the clamp adapter and light coupling may adopt any suitable orientation.

Figure 26:
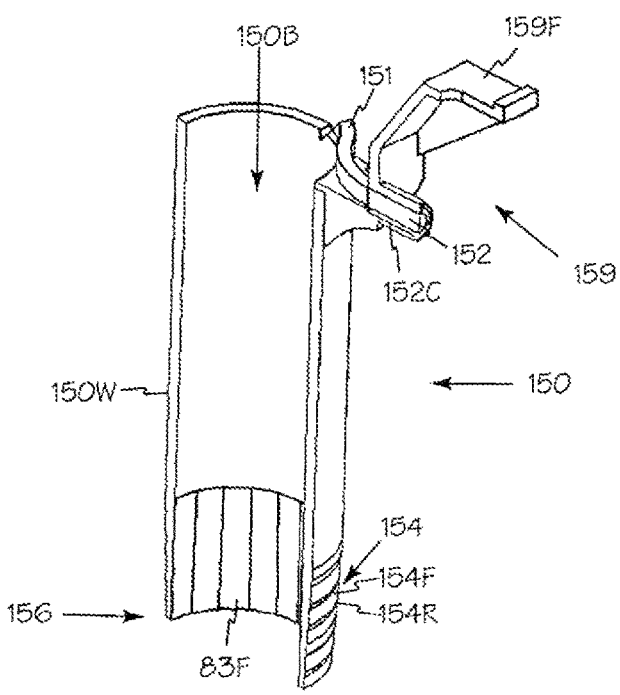
FIG. 26 is a cutaway view of the optical waveguide of FIG. 25.

FIG. 26 illustrates vertical facets 83F within the distal end for disrupting the light spiraling within the waveguide. Circumferential light extraction structures 154 may include stepped facets such as facets 154F and risers such as riser 154R on the outside tube wall 150W. The "riser" section of the stepped facet section 154R is angled so that it may slide against tissue without damaging the tissue. Steps may be uniform or non-uniform depending on the light directional control desired. The steps may be designed to directly light substantially inwards and toward the bottom of the tube or some distance from the bottom of the tube, or they may be designed to direct light toward the outside of the tube, or both.

Circumferential light extraction structures such as structures 154 may be facets or may be other geometries, such as parabolas. Circumferential light extraction structures coupled with light directing structures that provide circumferentially distributed light to the extraction structures provide circumferential illumination. Since tools entering the interior of the tube now have light shining on them from all sides, the tools do not cast any shadows within the cone of illumination emitted by the cannula. The circumferential illumination from a cylindrical waveguide creates a generally uniform cone of light that minimizes shadows, e.g., from instruments, creating substantially shadowless illumination in the surgical field below the tubular waveguide.

Cannula 150 of FIGS. 27-30 is illustrated without clamp flange/holder 159 in place. Input arms 151 and 153 are offset above proximal surface 161 by a distance 162 and end in angled reflector surface 158 that partially extends down distance 160 into the tube wall. The offset controls the light entering waveguide 150 and restricts light entering to input structure 165. Reflector surface 158 serves to direct light orthogonally from the horizontal input and down into the tube wall, also causing the light to spread around the circumference of the tube wall by the time the light reaches the distal or lower part of the tube. Reflector surfaces such as surface 158 may be a flat surface, an arced surface, or a series of interconnected surfaces and may also end at the top of the tube wall.

Reflector surface 158 may be treated, e.g., a reflective or metalized coating or an applied reflective film, to enhance reflection.

Air gaps may be used to isolate the light-conducting pathway in any suitable connector. Waveguide 150 of FIG. 29 includes male connector 148C that has been integrated with waveguide tube wall 157 via bracket 147. This allows connector 148C to be molded with the waveguide and not attached as a separate part, such as standard light connector 152C shown in FIG. 25. A separate connector introduces tolerance concerns into the system that may result in reduced coupling efficiency between a fiber optic cable output and waveguide input 149 because the two parts may not be aligned correctly. Molding the connector and the waveguide input as one piece substantially reduces the chance of misalignment and thereby increases coupling efficiency.

FIG. 30 is a front view looking into the input of connector 148C. Air gaps 146 are maintained around waveguide input 149 to isolate the light-conducting pathway. One or more small zones of contact such as contact zone 146C may be maintained, essentially bridging connector 148C and input 149 with a small amount of material, to add strength and stability to the system while resulting in minimum light loss in the contact zone.

Figure 31:
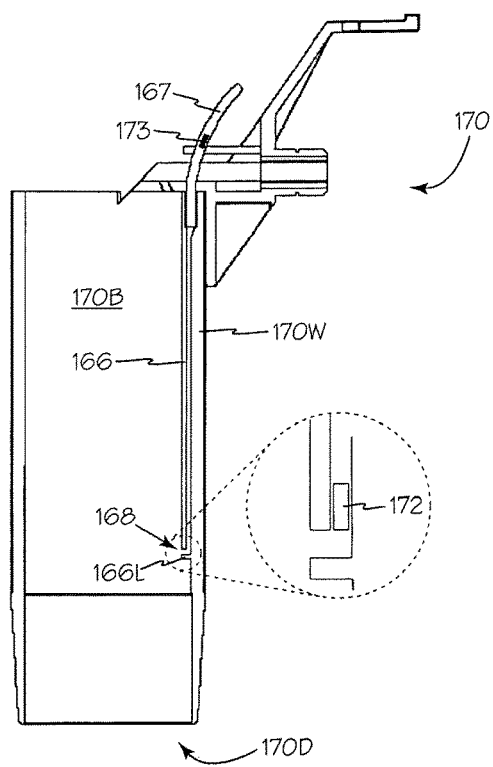
FIG. 31 is a cutaway view of the optical waveguide of FIG. 25 with a ventilation path added.

Referring now to FIG. 31, structure 166 along the inside wall may be used for suction for smoke evacuation and or ventilation. Smoke from an electrosurgical knife may obscure the surgeons view until the smoke dissipates. A ventilation tube such as tube 167 may be attached to the top of structure 166 to engage the suction structure and provide a source of suction or vacuum. The bottom of suction structure 166 may be as shown opening into working channel 170B orthogonal to wall 170W or it may open directly toward the bottom or distal end 170D by removing lower lip 166L. The former is preferred to reduce the chance that debris is sucked into the suction structure thereby blocking it. One or more additional tubes may also be positioned to inject air into the cannula bore, angled along the walls to create a vortex-like air flow that draws smoke toward the side walls where it can then be evacuated, said air flow serving to clear the smoke sooner from the center of the tube where it may obscure vision.

Small filters such as debris filter 172 may be included in or near suction input 168 to block debris. The lower suction opening, input 168, is preferred to be as close to distal end 170D of illuminated waveguide 170 as practical, while not interfering with the optical structures, in order to evacuate smoke from electrocautery as soon as possible. Multiple suction openings may be provided along the vertical channel of the suction section, but these ports should be sized differently, smallest at the top and largest at the bottom so that there is sufficient suction at the bottom port. The suction ports and channel should be designed to minimize turbulence that contributes to noise. Multiple suction structures may be provided. A shelf in clamp flange/holder may help secure suction tubing to suction source. Suction tubing 167 or suction structure 166 in tube 170 may also include one or more air filters 173, e.g., charcoal filters, to remove the smell of the smoke and or other airborne impurities.

Figure 32:
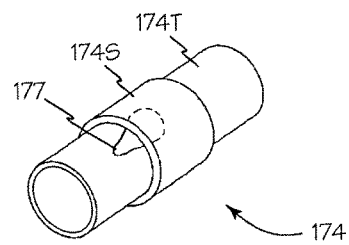
FIG. 32 is a perspective view of a ventilation controller.
Figure 33:
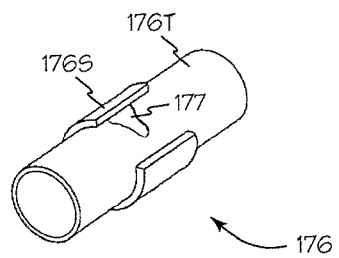
FIG. 33 is a perspective view of an alternate ventilation controller.

FIGS. 32 and 33 illustrate details of suction tube controls 174 and 176 with sliders 174S and 176S over a tear drop shaped opening 177 to control the amount of vacuum or suction. The irregular shape of openings 177 allows finer control over amount of vacuum over a constant shape opening like a rectangular or oblong opening. Any other suitable irregular may also be used. FIG. 32 shows slider 174S engaged to allow some suction. Slider 174S is made to go all the way around tube 174T with a friction fit. A slider such as sliders 174S or 176S may be moved completely off of opening 177 to stop suction. FIG. 33 shows slider 176S with a section removed allowing slider 176S to be simply rotated to expose opening 177 completely to turn off suction. For control 176, opening 177 can be rotated 90° relative to the orientation of opening 177 in control 174. The orientation of opening 177 in control 176 enables control of suction by simply rotating slider 176S rather than sliding it up and down as in control 174.

Figure 34:
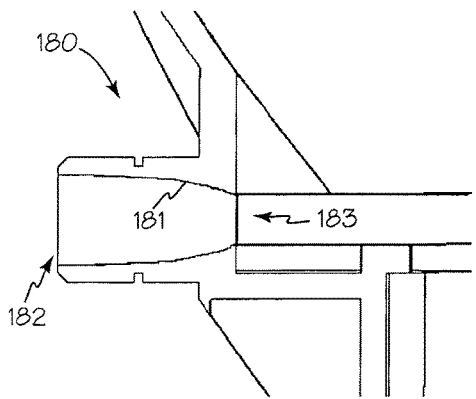
FIG. 34 is a cross-section of a light coupling for the optical waveguide of FIG. 25.
Figure 35A:
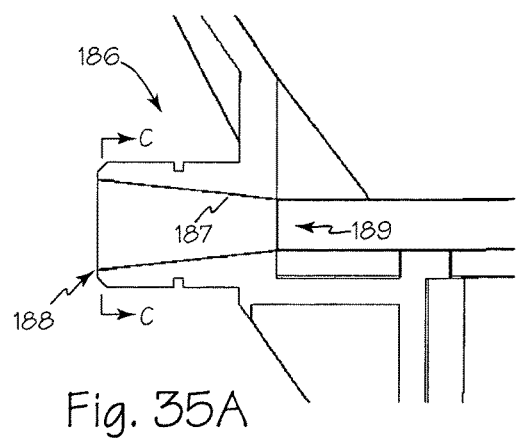
FIG. 35A is a cross-section of an alternate light coupling for the optical waveguide of FIG. 25.

Referring now to FIG. 34, input coupling 180 may incorporate compound parabolic concentrator 181 or similarly functioning device, such as optical taper 187 in FIG. 35A, whose input 182 is sized to match the largest fiber bundle, which is typically 5 or 6 mm in diameter, but whose output 183 is coupled to a smaller waveguide thickness, e.g., 3 or 5 mm. Such a device could be hidden in the connector of the waveguide device, e.g., inside of an ACMI connector or other suitable device.

These devices are governed by an equation that relates input and output area to the numerical aperture of the light entering and exiting the CPC or taper device. Specifically, the area times the numerical aperture of the input must equal the area times the numerical aperture of the output. This means that in going from a larger area input such as input 182 to a smaller area output such as output 183 to inject light into the waveguide, the numerical aperture at the output will increase thereby increasing the angles of the light entering the waveguide. Larger light angles are more difficult to control inside of the waveguide, resulting in greater light loss in the waveguide and increasing design complexity and cost. Thus, the numerical aperture of an input coupling such as coupling 180 or 186 should match or be less than the numerical aperture of the waveguide. Any other suitable method may be employed for enhancing light coupling efficiency to a fiber bundle cable while preserving etendue.

Figure 35B:
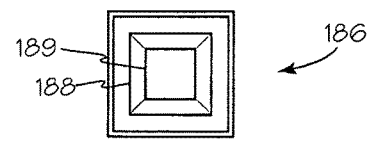
FIG. 35B is a cross section of the alternate light coupling of FIG. 35A taken along C-C.

Input 188 of optical taper coupling 186 of FIGS. 35A and 35B provides a significant improvement in input coupling occurs by using a square input coupler on the waveguide that couples to a typical, round fiber bundle cable. The increase in coupling surface area results in improved light coupling for a variety of fiber sizes without the effect on numerical aperture. For example, going from a 4 mm round coupler to a 4 mm square coupler results in 27% more surface area for coupling to a fiber bundle. If these round and square coupling faces are coupled to a 5 mm diameter fiber bundle, the percent of the 5 mm bundle that remains uncoupled is 36% with the round coupler, but is only 18% with the square coupler. This reduces the light lost by half while having no effect on the numerical aperture of the light going into the waveguide from the coupling face. The input square should be sized as close as practical to the maximum fiber bundle diameter expected. For example, if a 3 mm input is used to couple to a 5 mm fiber bundle, then the square input provides only a 10% improvement in coupling efficiency over a round input. A further improvement is made by shaping the optical fibers in the fiber bundle cable to match the square input of the waveguide so that the capture and dispersion of light in the waveguide is optimized. Similarly, any suitable index matching material may also be used, such as an index matching gel, to improve input coupling.

Figure 36A:
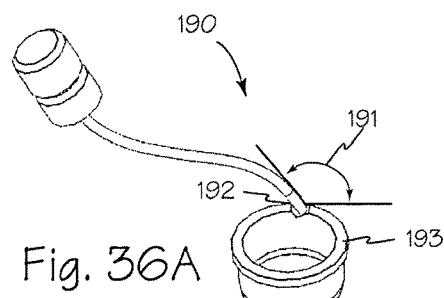
FIG. 36A is a perspective view of an ear speculum style optical waveguide.
Figure 36B:
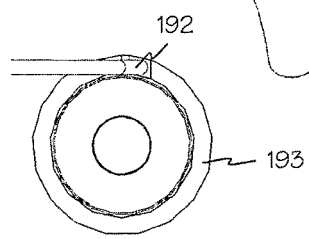
FIG. 36B is a top view of the ear speculum style optical waveguide of FIG. 36A.

FIGS. 36A and 36B illustrate an illumination waveguide configured as ear speculum 190. Input 192 is through proximal edge 193 with an angle 191 selected to control the angle of circulation of the light within the waveguide. Light enters the larger diameter upper portion and exits from at least one light extraction structure at or near the smaller diameter lower portion. The walls of the waveguide are preferably curved, but may adopt any other suitable geometry.

Figure 37A:
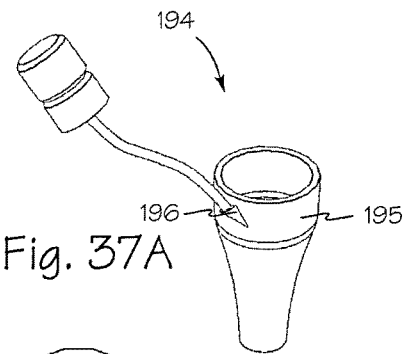
FIG. 37A is a perspective view of an ear speculum style optical waveguide with a side entry light coupling.
Figure 37B:
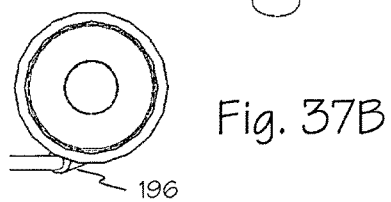
FIG. 37B is a top view of the ear speculum style optical waveguide of FIG. 37A.
Figure 38A:
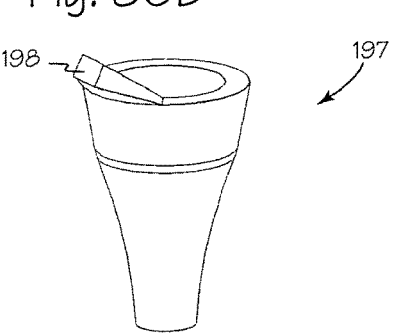
FIG. 38A is a perspective view of another alternate ear speculum style optical waveguide.
Figure 38B:
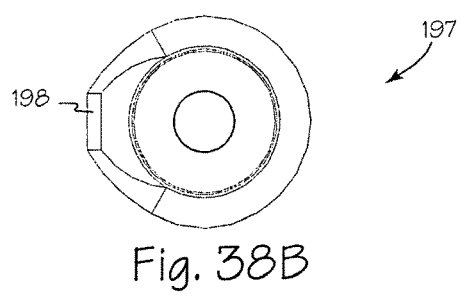
FIG. 38B is a top view of the ear speculum style optical waveguide of FIG. 38A.
Figure 40:
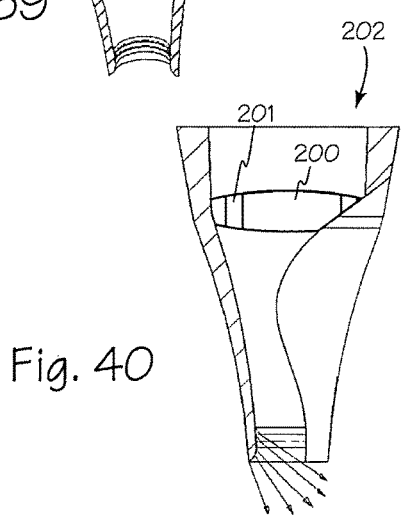
FIG. 40 is a cutaway view of the optical waveguide of FIG. 36A.

Alternatively, light input 196 may engage sidewall 195 of waveguide 194 as illustrated in FIGS. 37A and 37B. In an input configuration similar to the input of the cannula of FIG. 18 or 25, illumination waveguide 197 of FIGS. 38A, 38B and 39 may include a bifurcated input 198 that may include a beam directing prism as described for FIG. 11C.

Figure 39:
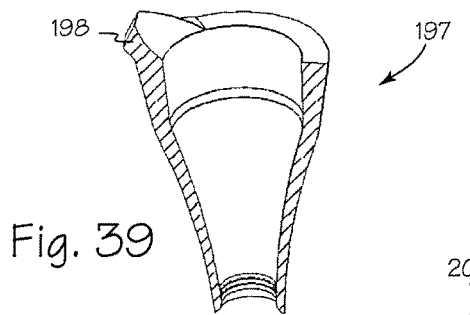
FIG. 39 is a cutaway view of the optical waveguide of FIG. 38A.

In the cutaway view of FIG. 39 one or more optical elements such as lens 200 may also be included in waveguide 202. Optical elements such as lens 200 may also include one or more ports such as port 201 to enable access for the insertion of tools, fluid, suction or any other suitable necessity.

Waveguide 210 of FIGS. 41 and 42 may be split open during surgery to permit greater access to the surgical field. Waveguide 210 may be rigid optical material, e.g., acrylic or polycarbonate, or may be flexible optical material, e.g., silicone, or may incorporate both flexible and rigid elements, e.g. a silicone waveguide hinge over-molded to an upper and lower rigid acrylic waveguide. Light input channels 211 and 213 may be split and fed through a fiber "Y" or may be comprised entirely of optical fibers. Fibers may be embedded into the wall of the wave-guide all the way to lower portion 210L that may incorporate light extraction structures. Waveguide 210 is fully split front and back from the top to about ½-⅔ of tube by slots 214 and 216. Alternatively, a waveguide may be split all the way to lower portion 210L. Lower portion 210L is scored inside and out with scoring such as score 218. The scoring operates to redirect light stuck circling the tube. The bottom element 220 is pre-split in half along edge 221 and may be glued or otherwise secured in a waveguide such as waveguide 210. The planar shape of element 220 permits viewing through bottom element 220 and allows light to shine through. Alternatively, element 220 may also adopt any other suitable geometry such as rounded to form a lens. Because of the interface with the tube along edge 222 very little light is conducted into element 220. Hole 223 enables a surgical screw or other suitable connector to engage through the bottom of waveguide 210 to a surgical site. Splitting waveguide 210 and bottom 220 frees the waveguide elements from the connector, and permits the waveguide elements to be removed from the surgical site. While at least one light extraction structure is preferably located in lower portion 210L on each tube half, the at least one extraction structure may be located on only one half or may be located further up the tube, e.g., near the end of split 216 and or split 214.

Figure 43:
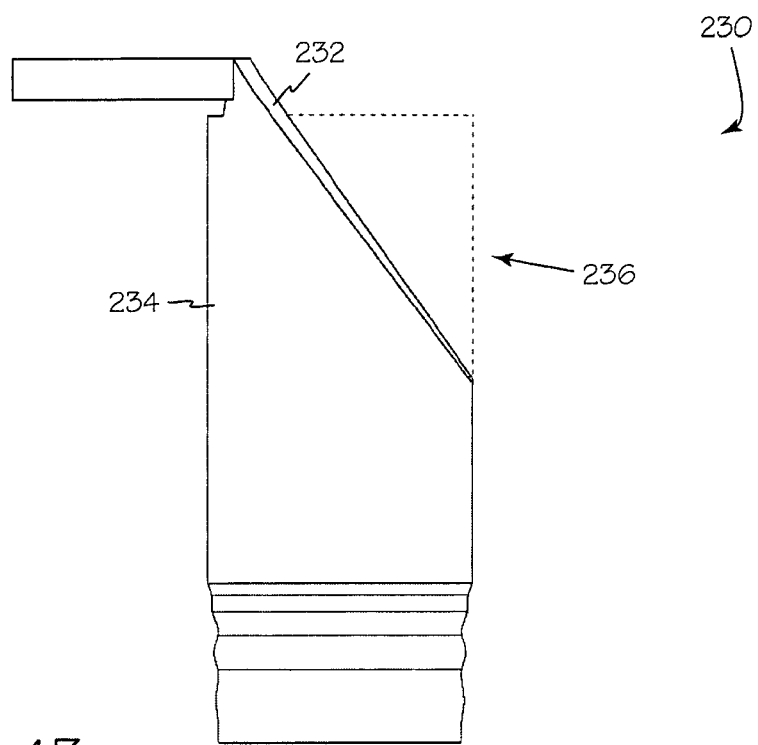
FIG. 43 is a cutaway view of an optical waveguide with an extended reflecting surface.

Waveguide 230 in FIG. 43 has reflector face 232 extending down to the opposite side of tube waveguide 234, effectively removing material 236. Extended reflector face 232 serves to direct light circumferentially around the tube wall. This opens up the waveguide to provide improved access to the surgical space. In addition, it offers the opportunity to replace removed material 236 with more durable material to improve strength and or provide the clamp flange holder function and or to provide mounting for other devices, such as a CCD camera.

Illuminated retractors such as cannula, waveguides, tubes and or sheaths may also benefit from extendable skirts or segments to prevent tissue encroaching on a surgical site. The extendable elements may also include interface surfaces to introduce light into the elements to enhance surgical site illumination and or provide off axis illumination to enhance shadows for better depth perception and tissue discrimination.

Figure 44:
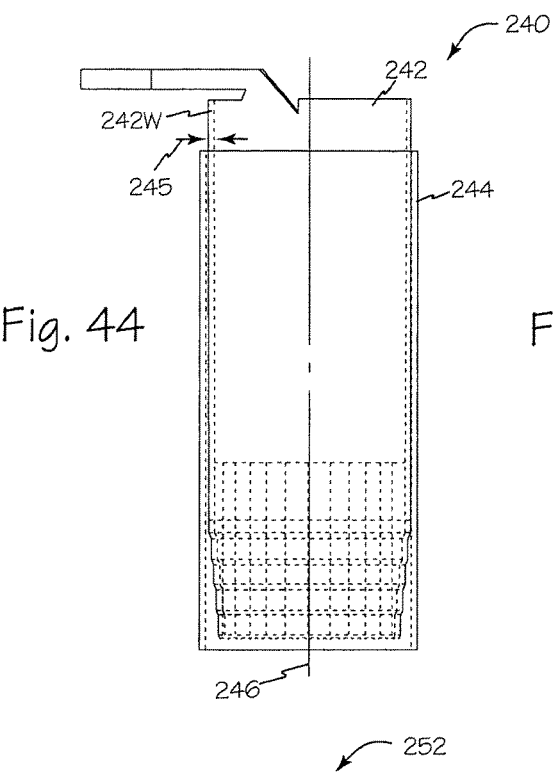
FIG. 44 is a side view of a combination cannula sleeve and optical waveguide.
Figure 45:
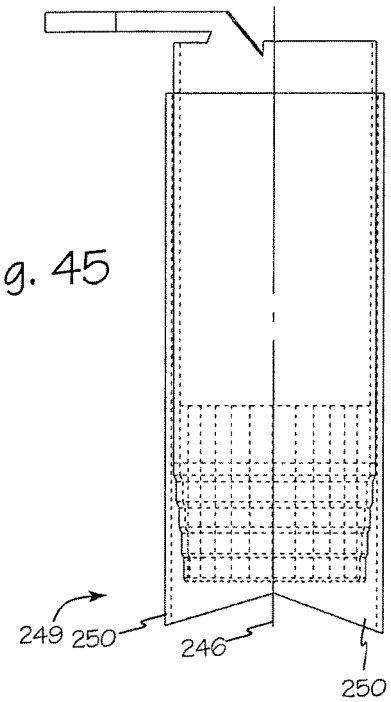
FIG. 45 is a side view of a combination optical waveguide and cannula sleeve with extended elements.
Figure 46:
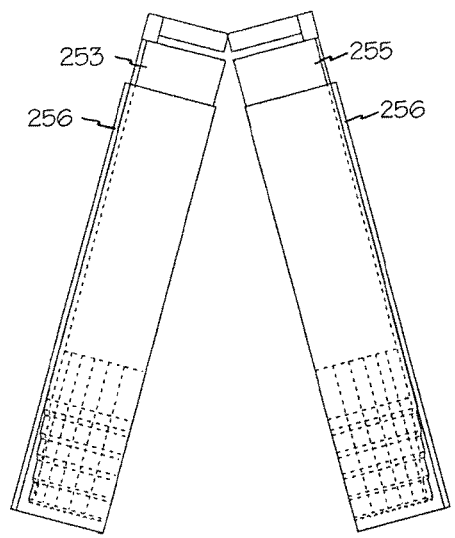
FIG. 46 is a side view of a split combination optical waveguide and cannula sleeve.
Figure 47:
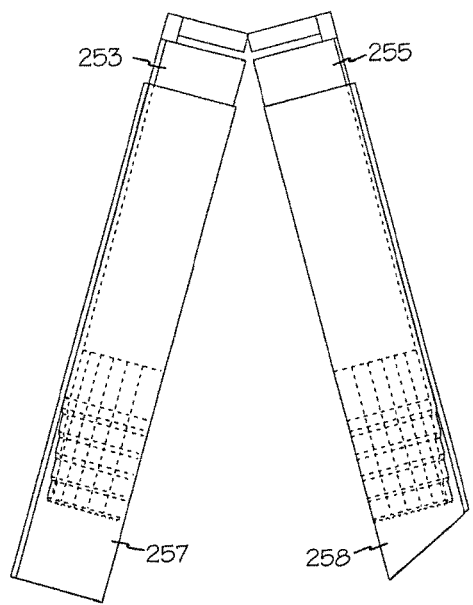
FIG. 47 is a side view of a split combination optical waveguide and cannula sleeve with extended elements.
Figure 48:
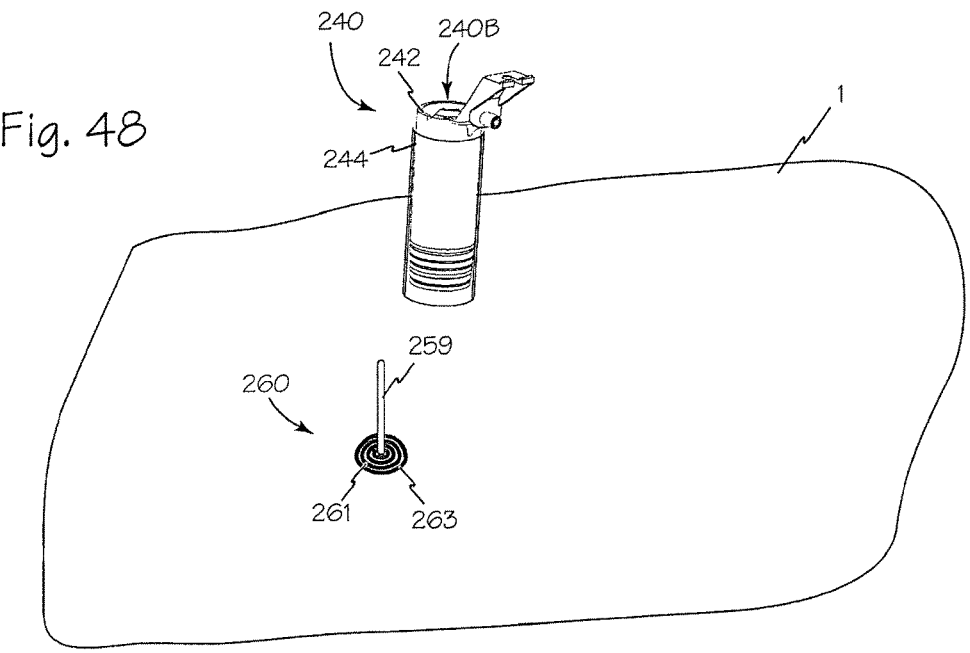
FIGS. 48 and 49 are perspective views of a cannula.
Figure 49:
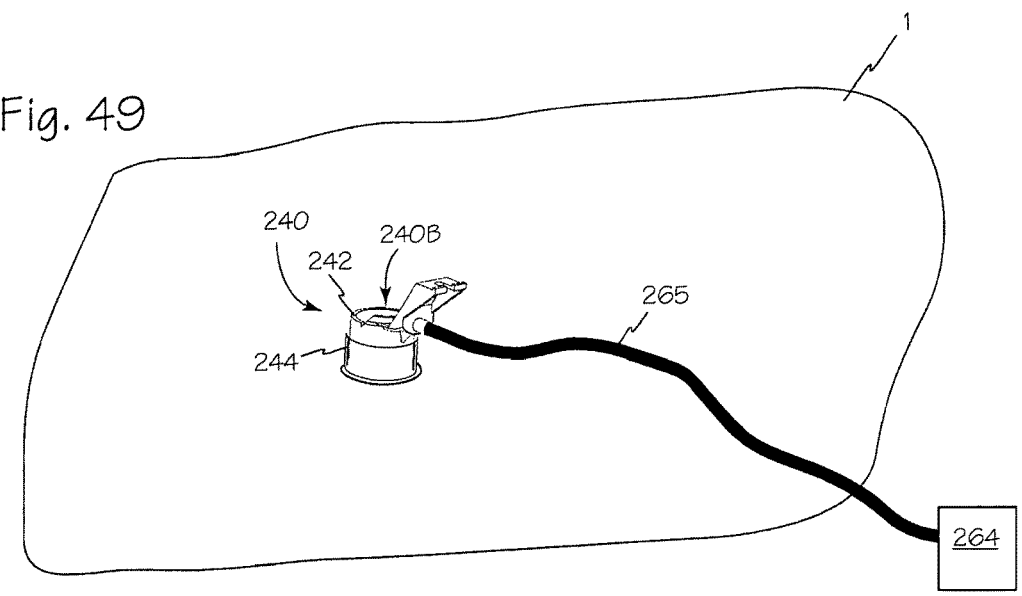

Combination cannula 240 includes waveguide cannula 242 and cannula sleeve 244 as illustrated in FIG. 44. Waveguide cannula 242 conducts light into a surgical space similar to illumination waveguide 150, illumination waveguide 170 or waveguide 230 as discussed above. Cannula sleeve 244 slides over waveguide cannula 242 and provides mechanical strength for retracting tissue. Waveguide cannula 242 may be made with wall 242W thinner than the walls of illumination waveguide 150, illumination waveguide 170 or waveguide 230 to allow the combined waveguide cannula and cannula sleeve to be used together without exceeding wall thickness 150W as shown in FIG. 27.

The illuminated retractors as discussed above may also be made extendable or telescoping to enable a varying depths of surgery with a single thus device minimizing hospital inventory. The illuminating cannulas discussed may also be formed as an illuminating drill guide, either as a tube or as two half tubes, that may be used to hold and guide drill or burr tip while also providing illumination of the area being worked on.

An optical waveguide may also operate as a cannula providing irrigation, suction, ventilation or other suitable services for medical applications. Suction may be provided via one or more passages within the structure of the waveguide or cannula. The suction paths or passages may also include any suitable filter media such as charcoal.

An optical waveguide may provide illumination and at the same time perform as a surgical instrument. Other than rigid endoscopes, devices such as trocars, obturators, retractors, may all be made from waveguide material. Devices, such as laryngoscope blades can be made out of waveguide material and thus be self illuminating thus eliminating any need for fiber optics. Use of one or more illumination sources above a surgical field inside the body may provide suitable illumination to generate shadows from the surgical instruments and thus provide visual feedback for the surgeons regarding instrument orientation and improved tissue discrimination.

An optical waveguide may also include one or more coupling lenses may be used to couple light into the optical waveguide. The lenses or other suitable structure may adopt any suitable geometry such as for example spherical, cylindrical, aspherical and or non-symmetrical geometries. If a light source having a wide output angle such as one or more LEDs is used, a more complex lens system such as an asphere may be used to optimize light coupling.

One or more faces of an optical waveguide may include a predetermined micro structured pattern. Different optical light output shapes or light output directions may be achieved by creating specific structured surfaces or patterns. It is also possible to specify microstructured surfaces to deflect light as well as focus it into a particular shape. One or more microstructures may be applied to the back and or the front of a refractive element to deflect the beam as well as shape it. Microstructure surfaces may also be combined with one or more air gaps and or conventional surface shaping to achieve desired optical performance. Optical fiber typically has a highly Gaussian output distribution that creates a small, bright spot of light that may not be suitable for visualization of a broad surgical area. The implementation of microstructures may create a broader, more uniform distribution of light thereby allowing comfortable viewing of a broader surgical area.

One or more surfaces in an optical waveguide sheath or adapters or connectors may be polarized using any suitable technique such as micro-optic structure, thin film coating or other. Use of polarized light in a surgical environment may provide superior illumination and coupled with the use of complementary polarized coatings on viewing devices such as cameras or surgeon's glasses may reduce reflected glare providing less visual distortion and more accurate color rendering of the surgical site. One or more surfaces of an optical waveguide sheath may also include light filtering elements to emit light of one or more frequencies that may enhance visualization of specific tissues.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. A method for creating and illuminating a surgical field, said method comprising:
   retracting a patient's tissue to determine a surgical field;
   introducing a light waveguide cannula to the surgical field, the light waveguide cannula having a proximal-most end, a distal end, and a central bore extending between the proximal-most end and the distal end, wherein the light waveguide cannula is configured as a single generally uniform light transmitting element, wherein one or more light conducting conduits are optically coupled to the light waveguide cannula so as to introduce light from a light source into the light waveguide cannula, and
   advancing a surgical instrument through the central bore toward the surgical field;
   introducing the light into the proximal-most end of the light waveguide cannula, wherein introducing the light comprises dividing the light from the one or more light conducting conduits into a plurality of arms of the light waveguide cannula that direct the light into the light waveguide cannula, the light being introduced circumferentially therearound, wherein the plurality of arms are entirely separate from each other at the proximal-most end of the light waveguide cannula; and
   circumferentially illuminating the surgical field with the light waveguide cannula.

2. The method of claim 1, wherein the one or more light conducting conduits are movably coupled to the light waveguide cannula so that the light waveguide cannula can rotate independently relative to the one or more light conducting conduits, the method further comprising rotating the one or more light conducting conduits without rotating the light waveguide cannula.

3. The method of claim 2, wherein rotating the one or more light conducting conduits comprises rotating the one or more light conducting conduits about a longitudinal axis of the light waveguide cannula.

4. The method of claim 1, wherein circumferentially illuminating the surgical field with the light waveguide cannula comprises extracting the light into the central bore proximal of the distal end.

5. The method of claim 1, wherein the plurality of arms are monolithic with the light waveguide cannula.

6. A system for illuminating a surgical field, said system comprising:
   a light waveguide cannula;
   a light conduction conduit for conducting light to the light waveguide cannula, the light waveguide cannula having a proximal end, a distal end, and a central bore extending between the proximal end and the distal end, the central bore being sized to accommodate one or more surgical instruments inserted from the proximal end and passing out through the distal end into the surgical field, wherein the light waveguide cannula is configured as a single generally uniform light transmitting element; and
   a light input connector adapted to optically couple the light conduction conduit to the proximal end of the light waveguide cannula and to introduce light from the light conduction conduit into the proximal end of the light waveguide cannula,
   wherein the light input connector divides into a plurality of arms that direct the light into the light waveguide cannula and circumferentially around the light waveguide cannula,
   wherein the plurality of arms are entirely separate from each other at the proximal end of the light waveguide cannula, and
   wherein the distal end of the light waveguide cannula comprises a light extraction structure for directing light from the light waveguide cannula into the surgical field.

7. The system of claim 6, wherein the light conduction conduit comprises a rotatable ring adapted to couple to the light input connector.

8. The system of claim 6, wherein the light conduction conduit is independently rotatable about a longitudinal axis of the light waveguide cannula.

9. The system of claim 6, wherein the light extraction structure comprises one or more microstructures.

10. The system of claim 9, wherein the one or more microstructures are formed on a surface of the distal end of the light waveguide cannula.

11. The system of claim 10, wherein the one or more microstructures are formed on an outer surface of the distal end of the light waveguide cannula.

12. The system of claim 9, wherein the one or more microstructures are arranged circumferentially around the distal end of the light waveguide cannula.

13. The system of claim 9, wherein the one or more microstructures comprise one or more facets formed at an obtuse angle to an adjacent distal surface of the distal end of the light waveguide cannula.

14. The system of claim 13, wherein the one or more facets comprise a plurality of stepped facets.

15. The system of claim 13, wherein the plurality of stepped facets have a uniform size.

16. The system of claim 6, wherein the plurality of arms are monolithic with the light waveguide cannula.

17. The system of claim 6, wherein each arm is at least partially separated from the proximal end of the light waveguide cannula by a respective gap.

18. The system of claim 6, wherein the light extraction structure is configured to extract the light into the central bore proximal of the distal end.

19. A system for illuminating a surgical field, said system comprising:
   a light waveguide cannula;
   a light conduction conduit for conducting light to the light waveguide cannula, the light waveguide cannula having a proximal end, a proximal-most end, a distal end, and a central bore extending between the proximal end and the distal end, the central bore being sized to accommodate one or more surgical instruments inserted from the proximal-most end and passing out through the distal end into the surgical field;
   a light input connector adapted to optically couple the light conduction conduit to the proximal end of the light waveguide cannula and to introduce light from the light conduction conduit into the proximal-most end of the light waveguide cannula; and
   a glare shield adapted to couple to the proximal end of the light waveguide cannula to block emissions of light from said proximal end,
   wherein the light input connector divides into a plurality of arms that direct the light into the light waveguide cannula, and
   wherein the light is introduced circumferentially therearound, and
   wherein the distal end of the light waveguide cannula comprises a light extraction structure for directing light from the light waveguide cannula into the surgical field.

20. The system of claim 19, wherein the glare shield defines an aperture sized to accommodate passage of the one or more surgical instruments therethrough when the glare shield is coupled to the proximal end of the light waveguide cannula.

* * * * *